United States Patent [19]

Jaynes et al.

[11] Patent Number: 5,811,654
[45] Date of Patent: Sep. 22, 1998

[54] PLANTS GENETICALLY ENHANCED FOR NUTRITIONAL QUALITY

[75] Inventors: Jesse M. Jaynes, Baton Rouge, La.;
Kenneth S. Derrick, Lake Alfred, Fla.

[73] Assignee: Louisiana State University, Baton Rouge, La.

[21] Appl. No.: 788,963

[22] Filed: Jan. 24, 1997

Related U.S. Application Data

[63] Continuation of Ser. No. 453,436, May 30, 1995, Pat. No. 5,597,945, which is a continuation of Ser. No. 152,933, Nov. 15, 1993, abandoned, which is a continuation of Ser. No. 994,085, Dec. 16, 1992, abandoned, which is a continuation of Ser. No. 817,950, Jan. 3, 1992, abandoned, which is a continuation of Ser. No. 646,449, Jan. 25, 1991, abandoned, which is a continuation of Ser. No. 115,941, Nov. 2, 1987, abandoned, which is a continuation-in-part of Ser. No. 889,225, Jul. 25, 1986, abandoned.

[51] Int. Cl.$^6$ ............................. A01H 5/00; C12N 15/29; C12N 15/82
[52] U.S. Cl. ..................... 800/205; 435/69.1; 435/172.3; 435/419
[58] Field of Search ........................... 800/205; 435/69.1, 435/172.3, 419

[56] References Cited

U.S. PATENT DOCUMENTS

| | | | |
|---|---|---|---|
| 3,911,110 | 10/1975 | Smirnoff | 424/93 |
| 4,109,018 | 8/1978 | Thompson | 426/62 |
| 4,355,104 | 10/1982 | Hultmark et al. | 435/70 |
| 4,520,016 | 5/1985 | Hultmark et al. | 514/12 |
| 4,579,821 | 4/1986 | Palmiter et al. | 435/172.3 |
| 4,643,988 | 2/1987 | Segrest et al. | 514/12 |
| 4,704,362 | 11/1987 | Itakura et al. | 435/253 |
| 4,784,861 | 11/1988 | Gori | 426/74 |
| 4,844,924 | 7/1989 | Stanley | 426/258 |
| 4,962,028 | 10/1990 | Bedbrook et al. | 435/172.3 |
| 5,003,045 | 3/1991 | Hoffman | 530/378 |

FOREIGN PATENT DOCUMENTS

| | | |
|---|---|---|
| 0157351 | 10/1985 | Germany . |
| 0182278 | 5/1986 | Germany . |
| 0043075 | 6/1992 | Germany . |
| 1311375 | 3/1973 | United Kingdom . |
| 063949 | 11/1982 | United Kingdom . |
| 117600 | 9/1984 | United Kingdom . |
| 0142924 | 5/1985 | United Kingdom . |
| 145338 | 6/1985 | United Kingdom . |
| 0184288 | 6/1986 | United Kingdom . |
| 140556 | 5/1995 | United Kingdom . |
| 8604356 | 7/1986 | WIPO . |
| 8800976 | 2/1988 | WIPO . |

OTHER PUBLICATIONS

Abel, Patricia, *Science*, "Delay of Disease Development in Transgenic Plants That Express the Tobacco Mosaic Virus Coat Protein Gene", 1986, 232:738–743.

Anderson, Lucy, *J. Cell Sci.*, "Protein Synthesis and Uptake by Isolated Cecropia Oocytes", 1971, 8:735–750.

Andreau, D., et al., *Biochemistry*, "N–Terminal Analogues of Cecropin A: Synthesis, Antibacterial Activity, and Conformational Properties", 1985, 24:1683–1688.

Barton, K. A., *Science*, "Prospects in Plant Genetic Engineering", Feb. 1983, 219:671–676.

Beachy, R. *Genetic Tech News*, "Virus Genes Might Protect Plants From Disease", 1985, 8:4–5.

Bernheimer, A.W., et al., *Biochimica et Biophysica Acta*, "Interactions between Membranes and Cytolytic Peptides", 1986, 86:123–141.

Bessler, W. G., *Biochemical and Biophysical Research Communications*, "Interaction of Membrane Modifying Peptide Antibiotics from *Trichoderma viride* with Leukocytes", 1979, 87:99–105.

Blasi, Udo, *Gen Virol.*, "Influence of C–terminal Modifications of Φ X174 Lysis Gene E on its Lysis–inducing Properties", 1985, 66:1209–1213.

Boller, Thomas, *UCLA Symp. Mol. Cell. Biol.*, Newser, "Induction of Hydrolases as a Defense Reaction Against Pathogens", 1985 (Cell. Mol. Biol. Plant Stress).

Boman, H. G., *Development and Comparative Immunology*, On the Primary Structures of Lysozyme, Cecropins and Attacins from *Hyalophora cecropia*, 1985, 9:551–558.

Boman, H.G., *Ann. Rev. Microbiol.*, "Cell–Free Immunity in Insects", 1987 41:103–26.

Bowman, John E., *American Potato Journal*, "Resistance to *Pseudomonas solancearum* in Potato: Infectivity Titrations in Relation to Multiplication and Spread of the Pathogen", 1982, 59:155–164.

Brillinger, G. U., *Arch Microbiol*, "Metabolic Products of Microorganisms 181\*. Chitin Synthase from Fungi, a Test Model for Substances with Insecticidal Properties", 1979, 121:71–74.

Buckley, K.J., *Mol. Gen. Genet*, "Lytic Activity Localized to Membrane–spanning Region of ΦX174 E Protein", 1986, 204:120–125.

*Central Patents Index*, Basic Abstracts Journal, Section C, AGDOC, Dec. 1977, abstract 91378, Derwent Publications Ltd., (Japan) Plywood Techn. Nov. 29, 1977 "Making Lumber Insect Repellent by Permeating with Aqueous Solution Containing Amylase, and Rinsing with Water".

(List continued on next page.)

*Primary Examiner*—David T. Fox
*Attorney, Agent, or Firm*—Rothwell, Figg, Ernst & Kurz, p.c.

[57] ABSTRACT

Plant transformants having an expressible heterologous gene for an antimicrobial agent for disease resistance and/or a protein high in limiting essential amino acid content for enhanced nutritional quality. Monocots, dicots and gymnosperms are genetically enhanced for disease resistance to express a lytic peptide such as cecropin, attacin or lysozyme, or an antiviral antisense micRNA. The nutritional quality of plants cultivated for food is enhanced by a gene expressing a protein containing 25–60 weight percent of methionine, lysine, tryptophan, threonine and isoleucine. Methods for obtaining such transformants, novel expressing vectors, novel proteins high in essential amino acids, and novel lytic peptides are also disclosed.

6 Claims, 9 Drawing Sheets

OTHER PUBLICATIONS

*Central Patents Index,* Basic Abstracts Journal, Section C, AGDOC, Jul. 1979, abstract 53721, Derwent Publications (Mitsui Petrochem Ind. K.K.) Dec. 6, 1979 "Antimicrobia Enzyme prepared by Culturing Bacillus Bacteria".

Chen, Hao–Chia, FEBS LETTERS, "Synthetic Magainin Analogues with Improved Antimicrobial Activity", 1988, 236:462–466.

Chilton, Mary–Dell, *Scientific American,* A Vector for Introducing New Genes into Plants, 1983, 248:50–59.

Coleman, Jack, *Cell,* "The use of RNAs Complementary to Specific mRNAs to Regulate the Expression of Individual Bacterial Genes", 37:429–436.

Comai, L., *Plasmid,* "A New Technique for Genetic Engineering of *Agrobacterium* Ti Plasmid", 1983 10:21–30.

Comai, L., *Nature,* "Expression in Plants of a Mutant AroA Gene from *Salmonella typhimurium* Confers Tolerance to Glyphosate", 1985, 317:741–744.

Daum, Gunter, *Biochem. And Biophys. Res. Comm.,* Reversible Activation and Inactivation of Phosphofructokinase from *Ascaris suum* by the Action of Tissue–Homologous Protein Phosphorylating and Dephosphorylating Enzymes, 1986 136:215–221.

Dean, Caroline, *UCLA Symp.,* Newser, "Expression of Petunia rbcs Gene Fusions in Transformed Tobacco Plants", vol. 62, pp. 289–300, 2–8 Feb. 1987.

de la Pena, A., *Nature,* "Transgenic Rye Plants Obtained by Injecting DNA into Young Floral Tillers", 1987, 325:274–276.

Deshpande, M. V., *Journal of Scientific and Industrial Research,* "Enzymatic Degradation of Chitin & Its Biological Applications", 1986, 45:273–281.

Doel, M. T. *Nucleic Acids Research,* "The Expression in *E. coli* of Synthetic Repeating Polymeric Genes Encoding for Poly(L–aspartyl–L–phenylalanine)", 1980, 8:4575–4593.

Drummond, M., *Nature,* "Launching Genes Across Phylogentic Barriers", 1983, 303:198–199.

Drutz, D., *Basic & Clinical Immunology,* "Immunity & Infection", 1984, 197–201.

*Electroporation*—"Transfection of Mammalian Cells in Culture" 18–3:293–295.

Engstrom, A., *The EMBO Journal,* "Insect Immunity. The Primary Structure of the Antibacterial Protein Attacin F and its Relation to Two Native Attacins from *Hyalophora cecropia*", 1984, 3:2065–2070.

Engstrom, A., *The EMBO Journal,* "Amino Acid and cDNA Sequences of Lysozyme from *Hyalophora cecropia*", 1985, 4–2119–2122.

Fischoff, David A., *Bio/Technology,* "Insect Tolerant Transgenic Tomato Plants", 1987, 5:807–813.

Fraley, R. T., *Proc. Nat. Acad. Sci. USA,* "Expression of Bacterial Genes in Plant Cells", 80:4803–4807, Aug. 1983.

Freeman, J. P., *Plant & Cell Physiol,* "A Comparison of Methods for Plasmid Delivery into Plant Protoplasts", 1984, 25(8):1353–1375.

French, E. R., *Phytopathology,* "Resistance to *Pseudomonas solanacearum* in Potato: Specificity and Temperature Sensitivity", 1982, 72:1408–1412.

Fromm, Michael, *Proc. Natl. Acada. Sci.,* Expression of Genes Transferred into Monocot and Dicot Plant Cells by Electroporation, 82:5824–5828.

Fromm, Michael, *Nature,* "Stable Transformation of Maize after Gene Transfer by Electroporation", 1986, 319:791–793.

Fuchs, R. L., *Applied and Environmental Microbiology,* "Cloning of a *Serratia marcescens* Gene Encoding Chitinase", 1986, 51:504–509.

Garcia, Lopez, *Biochem Genetics,* "Production of Lysozyme *Streptococcus pneumonia* in *Escherichia coli* by Recombinant DNA Technology", 1986, 106:190368d.

Garrett, Jinnie, *Mol. Gen. Genet.,* "Cell Lysis by Induction of Cloned Lambda Lysis Genes", 1981, 182:326–331.

Gaynor, John J., *Chemical Abstracts,* "Defense Genes in Bean Seedlings: Induction of Chitinase by Ethylene", 1986, 104:183450e.

Gelehrter, Thomas D., *Biochem. And Biophys. Res. Comm.,* "Stimulation of Monovalent Ion Fluxes and DNA Synthesis in 3T3 Cells by Melitin and Vasopressin is not Mediated by Phospholipid Deacylation",, 1980, 97:716–724.

Gibson, Bradford W., *The Journal of Biological Chemistry,* "Novel Peptide Fragments Originating from $PGL^a$ and the Caerulein and Xenopsin Precursors from *Xenopus laevis*", 1986, 261:5341–5349.

Gilboa, Eli, *Bio Techniques,* "Transfer and Expression of Cloned Genes Using Retroviral Vectors", 1986, 4:504–512.

Giovannini, Maria G., *Biochem. J.,* "Biosynthesis and Degradation of Peptides Derived from *Xenopus laevis* Prohormones", 1987, 243:113–120.

Goodman, Robert M., *Science,* "Gene Transfer in Crop Inprovement", 1987, 236:48–54.

Goy, P., *Agro. Division Report,* "Spectrum of Activity of 1 Synthetic Cecropin: In Vitro and In Vivo Tests", 12 F Report 89013xx, Oct. 18, 1989.

Hashimoto, H., *Appl. Microbiol Biotechnol,* "A Novel Method for Transformation of Intact Yeast Cells by Electroinjection of Plasmid DNA", (1985) 21:336–339.

Hibi, T., *J. Gen. Virol.,* "High Efficiency Electro–transfection of Tobacco Mesophyll Protoplasts with Tobacco Mosaic Virus RNA", 1986; 67:2037–2042.

Horsch, Robert B., *Science,* "Inheritance of Functional Foreign Genes in Plants", 1984, 223:496–498.

Horwitz, Marc, *Mammalian Hormones,* "Genetic Improvement of Chitinase Production by *Serratia marcescens*", 1985, 102:216038R.

Hultmark, D., *Eur. J. Biochem.,* Insect Immunity. Purification and Properties of Three Inducible Bactericidal Proteins from Hemolymph of Immunized Pupae of *Hyalophora cecropia,* 1980, 106:7–16.

Hultmark, D., *Eur. J. Biochem.,* "Insect Immunity: Isolation and Structure of Cecropin D Four Minor Antibacterial Components from Cecropia Pupae", 1982, 127–207–217.

Hultmark, D., *The EMBO Journal,* "Insect Immunity. Attacins, a Family of Antibacterial Proteins from *Hyalophora cecropia*", 1983, 2:571–576.

Iiauka, C., *Chemical Abstracts,* Oct. 1975, vol. 83, No. 17, p. 145, abstract 143033n "Herbicides".

Isamu, H. *Chemical Abstracts,* "Aricine as a Bactericide and Fungicide", vol. 97, p. 290, abstract 97:87036r, 1982.

Izant, J., *Cell,* "Inhibition of Thymidine Kinase Gene Expression by Anti–Sense RNA: A Molecular Approach to Genetic Analysis", 1984, 36:1007–1015.

Jaynes, J.M., Departments of Biochemistry, Vet Science and Animal Science, L.S.U. "In Vitro Effect of Novel lytic Peptides on *Plasmodium falciparum* and *Trypanosoma cruzi*" (date unknown).

Jaynes, J.M., et al *Appl. Microbiol. Biotechnol.,* "Construction and Expression of Synthetic DNA Fragments Coding for Polypeptides with Elevated Levels of Essential Amino Acids", 1985, 21:200–205.

Jaynes, J.M., *J. Cell Biochem.*, "Integrating and Expression of Viroid cDNAs in Plant Cells", 1986, (10 part C) p. 40.

Jaynes, J.M., et al. *Trend Biotechnol,* "Plant Protein Improvement by Genetic Engineering: Use of Synthetic Genes", 1986, 4(12):314–320.

Jaynes, J.M., *BioEssays,* "Increasing Bacterial Disease Resistance in Plants Utilizing Antibacterial Genes from Insects", Jun. 1987, 6:263–270.

Jones, Jonathon, *Journal of Cellular Biochemistry,* "Engineering Bacterial Chitinase Genes for Crop Protection", Abstract J. 30, 1986.

Kado, C.I., *Phytopathogenetic Prokaryotes,* "Prospectus for Genetic Engineering in Agriculture", vol. 2, Chapter 14, pp. 303–325, 1982.

Kamemoto, E., *Archives of Biochem. and Biophys.,* "Phosphofructokinase from *Fasciola hepatica*: Actication by Phosphorylation and other Regulatory Properties Distinct from the Mammalian Enzyme", Jun. 1987, 258:101–111.

Kangas, T. *Applied and Environmental Microbiology,* "Expression of a Proline–Enriched Protein in *Escherichia coli*", 1982, 43:629–635.

Kay, R., *Science,* "Duplication of CaMV 35S Promoter Sequences Creates a Strong Enhancer for Plant Genes", Jun. 1987, 236:1299–1302.

Kemp J.D., *Chemical Abstracts,* "Transfer of a Functional Gene via the Ti iPlasmid", vol. 101, No. 3, Jul. 1984, pp. 176–177, abstract 101:18452n.

Kockum, K., *The EMBO Journal,* "Insect Immunity. Isolation and Sequence of Two cDNA Clones Corresponding to Acidic and Basic Attacins from *Hyalophora cecropia*", 1984, 3:2071–2075.

Krens, F.A., *Nature,* "In vitro Trnasformation of Plant Protoplasts with Ti–plasmid DNA", 1982, 296:72–74.

Langridge, W., *Plant Cell Reports,* "Electric Field Mediated Stable Transformation of Carrot Protoplasts with Naked DNA", 1985, 4:355–359.

Lee, J. Y., *The EMBO Journal,* "Insect Immunity. Isolation of cDNA Clones Corresponding to Attacins and Immune Protein P4 from *Hyalophora cecropia*" 1983, 2:577–581.

Loesch–Fries, L., UCLA Symp. *Molec. Cell Biol.,* "Cloning of Alfalfa Mosiac Virus Coat Protein Gene and Anti–sense RNA into a Binary Vector and their Expressions in Transformed Tobacco Tissue", 1986, p. 41, abstract J 108.

Lorz, Horst, *Mol. Gen. Genet,* "Gene Transfer to Cereal Cells Mediated by Protoplast Transformation", 1985, 199:178–182.

Matthias, P., *Chemical Abstracts,* "Transient Expression of the Chicken Lysozyme Gene after Transfer into Human Cells", 1983, vol. 98, p. 147, abstract 98:12350a.

Merrifield, R.B., *Biochemistry,* "Synthesis of the Antibacterial Peptide Cecropin A(1–33)", 1982, 21:5020–5031.

Miyada, C. Garrett, *J. Bacteriol.,* "Five Mutations in the Promoter Region of the araBAD Operon of *Escherichi coli* B/r", 1983, 156:765–772.

Molano, Jesus, *The Journal of Biological Chemistry,* "An Endochitinase from Wheat Germ", 1979, 254:4901–4907.

Monreal, J., *Canadian Journal of Microbiology* (Ottawa), "The chitinase of *Serratia marcescens*", 1969, 15:689–696.

Murai, N., *Chemical Abstracts,* "T–DNA of pTi–15955 from *Agrobacterium tumefaciens* is Transcribed into a Minimum of Seven Polyadenylated RNA's in a Sunflower Crown Gall Tumor", 96:17513h, 1982.

Nakai, T. *Chemical Abstracts,* "Synthesis of Self–defense Substance Produced by Silkworm, Lepidopteran, and Related Peptides", 106:214351w, 1986.

Nakajima, Y., *Biological Chemistry,* "Interaction Between Liposomes and Sarcotoxin IA, a Potent Antibacterial Protein of *Sarcophaga peregrina* (Flesh Fly)", 1987, 26:1665–1669.

Nicolson, G., *The Journal of Cell Biology,* "Ultrastructural Localization of Lectin–Binding Sites on the Zonae Pellucidae and Plasma Membranes of Mammalian Eggs", 1975, 66:263–274.

Nitesche, W., *Theoretical and Applied Genetics,* "Chitinase as a Possible Resistance Factor for Higher Plants," vol. 65, No. 2, 1983.

Norrander, Jan M.,*Journal of Biotechnology,* "Manipulation and Expression of the Maize Zein Storage Proteins in *Escherichia coli*", 1985, 2:157–175.

Okada, K., *Plant Cell Physical,* "Introduction of Functional RNA into Plant Protoplasts by Electroporation", 1986, 27:619–626.

Okada, M., *Biochem. J.,* "Ionophore Activity of Sarcotoxin I, a Bactericidal Protein of *Sarcophaga peregrina*", 1985, 229:453–458.

Ou–Lee, T., *Botany,* "Expression of a Foreign Gene Linked to Either a plant–virus or a *Drosophila* Promoter, after Electroporation of Photoplasts of Rice, Wheat, and Sorghum", 1986, 83:6815–6819.

Palukaitis, P., *Plant–Microbe Interactions,* "A Model to Explain the Cross–Protection Phenomenon Shown by Plant Viruses and Viroids", 1984 pp. 420–429.

Pownall, H. J., *Biochem. And Biophys. Res. Comm.,* "The Helical Hydrophobic Moment Avoids Prolines in Phospholipid–binding Proteins", 1986, 139:202–208.

Potrykus, I., *Mol. Gen. Genet.,* "Direct Gene Transfer to Cells of a Graminaceous Monocot", 1985, 199:183–188.

Ream, L.W., *Science,* "Crown Gall Disease and Prospects for Genetic Manipulation of Plants", Nov. 1982, 218:854–859.

Ream, L.W., *Proc. Nat. Acad. Sci. USA,* "Multiple Mutations in the T Region of the *Agrobacterium tumefaciens* Tumor–inducing Plasmid", Mar. 1983, 80:1660–1664.

Rennell, D., *Virology,* "Phage P22 Lysis Genes: Nucleotide Sequences and Functional Relationships with T4 and X Genes", 1985, 143:280–289.

Sawazaki, T., *Chemical Abstracts,* "Enzymic fungicides", vol. 87, p. 160, abstract 87:79669c, 1977.

Shah, Dilip, *Science,* "Engineering Herbicide Tolerance in Transgenic Plants", 1986, 233:478–481.

Shiba, T., *Chemical Abstracts,* "Antimicrobial Peptides from Silkworm *Hemolymph*", 104:230430k, 1985.

Shillito, R.D., *Biotechnology,* "High Efficiency Direct Gene Transfer to Plants", 1985, 3:1099–1103.

Soto–Gil, R., "Cloning of *Vibrio harveyi* Chitinase and Chitoblast Genes in *Escherichia coli*," 1984, 209–223.

Steiner, H., *Nature,* "Sequence and Specificity of two Antibacterial Protein Involved in Insect Immunity", 1981, 292:246–248.

Uchimiya, H., *Mol. Gen. Genet.,* "Expression of a Foreign Gene in Callus Derived from DNA–treated Protoplats of Rice" (*Oryza sativa* L), 1986, 204:204–207.

Vaeck, M., *UCLA Symp. Mol. Cell. Biol.,* Newser, V. 48, Molecular Strategies for Crop Protection, "Engineering of Insect Resistant Plants Using a *B. Thuringiensis Gene*", 1986.

Van Hofsten, P., *Proc. Natl. Acad. Sci. USA,* "Molecular Cloning, cDNA Sequencing, and Chemical Synthesis of Cecropion B from *Hyalophora cecropia*", 1985, 82:2240–2243.

White, A., *Principles of Biochemistry, 6th ed.,* 1978, p. 708.

Wortman, A.T., *App and Environt'l Microbiol,* "Chitinase Determinants of *Vibrio vulnificus:* Gene cloning and Applications of a Chitnase Probe", 1986, 52:142–145.

Andreau, D., et al., *Proc. Natl. Acad. Sci.,* "Solid–phase synthesis of Cecropin A and Related Peptides", 1983, 80:6475–6479.

PLANTS GENETICALLY ENHANCED FOR NUTRITIONAL QUALITY

CROSS-REFERENCE TO RELATED APPLICATION

This is a continuation of U.S. Ser. No. 08/453,436, filed May 30, 1995, now U.S. Pat. No. 5,597,945, which is a continuation of U.S. Ser. No. 08/152,933, filed Nov. 15, 1993, now abandoned, which is a continuation of U.S. Ser. No. 07/994,085, filed Dec. 16, 1992, now abandoned, which is a continuation of U.S. Ser. No. 07/817,950, filed Jan. 3, 1992, now abandoned, which is a continuation of U.S. Ser. No. 07/646,449, filed Jan. 25, 1991, now abandoned, which is a continuation of U.S. Ser. No. 07/115,941, filed Nov. 2, 1987, now abandoned, which is a continuation-in-part of U.S. Ser. No. 06/889,225, filed Jul. 25, 1986, now abandoned.

FIELD OF THE INVENTION

The present invention relates to genetically enhanced plants, and particularly to gymnosperms, monocots and dicots genetically altered to express antifungal and antibacterial peptides and/or to express polypeptides which have high proportions of limiting essential amino acids.

BACKGROUND OF THE INVENTION

Many attempts have been made to obtain improved plants for cultivation through breeding programs. A conventional plant breeding program requires as much as ten years to develop a new variety. In addition to the initial hybridization step, several years are typically spent replanting successive generations in order to obtain homozygous plants. An alternative to a conventional plant breeding program is anther culturing in which anthers from one plant are used to pollinate the ovaries of another plant. However, many traits cannot be successfully introduced via such hybridization techniques since the genes for such traits are not found in breeds available for hybridization.

An alternative to hybridization is somaclonal variation. This technique involves the use of vegetative plant parts, such as callus tissue, as explant material. For example, callus that develops from vegetative explants of rice frequently regenerates plants which have genetic characteristics not found in the variety from which the explant was originally obtained. These somatic mutants occur at high frequencies, and the percentage of regenerated plants which differ from the starting variety exceeds, for example, 75 percent in rice. This technique is therefore useful for producing genetic variability. Again, however, there are limits to the extent of variation which can be obtained.

Development of plant genetic engineering began in the early 1940s when experiments were being carried out to determine the biological principle causing formation of crown gall tumors. The tumor-inducing principle was shown to be a bacterial plasmid from the infective organism *Agrobacterium tumefaciens*. This plasmid has since been characterized in much detail utilizing the currently available techniques of recombinant DNA technology. The bacterium elicits its response by inserting a small fragment of bacterial plasmid into the plant nucleus where it becomes incorporated and functions as a plant gene. This discovery opened the door to using Agrobacterium and its plasmids as vehicles to carry foreign DNA to the plant nucleus. There are, however, limitations to the application of this technique which include: (1) susceptibility to infection with the Agrobacterium plasmid and (2) available tissue culture technology for regeneration of the transformed plants. Thus, there are no successful reports on genetic engineering of monocots such as cereals with Agrobacterium plasmid vectors because of the general inability of Agrobacterium to infect monocots.

More recently, other techniques have been used to genetically transform monocots. For example, electroporation of protoplasts of rice, wheat and sorghum to obtain expression of a foreign gene was reported in Ou-Lee et al, *Botany*, vol. 83, pp. 6815–6819 (1986). Similar plant protoplast electroporation and electroinjection through cell walls and membranes have also been reported for other monocots, and dicots as well. See, Fromm et al, *Proc. Natl. Acad Sci USA*, vol. 82, pp. 5824–5828 (1985); Hibi et al, *J. Gen. Virol.*, vol. 67, pp. 2037–2042 (1986); Langridge et al, *Plant Cell Reports*, vol. 4, pp. 355–359 (1985); Fromm et al, *Nature*, vol. 319, pp 791–793; Shillito et al, *Bio/Technology*, vol. 3, pp. 1099–1103 (1985); and Okada et al, *Plant Cell Physiol.*, vol. 27, pp. 619–626 (1986). Similarly, direct and chemical-induced introduction of DNA into monocot and dicot cells has been disclosed. See, Lorz et al, *Mol. Gen. Genet.*, vol. 199, pp. 178–182 (1985); Potrykus et al, *Mol. Gen. Genet.*, vol. 199, pp 183–188 (1986); Uchimaya et al, *Mol. Gen. Genet.*, vol. 204, pp 204–207 (1986); Freeman et al, *Plant & Cell Physiol.*, vol. 25, no. 8, pp. 1353–1365 (1984); and Krens et al, *Nature*, vol. 296, pp. 72–74 (1986). Another technique of interest is the injection of DNA into young floral tillers of rye plants reported in de la Pena et al, *Nature*, vol. 325, pp. 274–276 (1987).

The agricultural production of major crops has long been significantly affected by insects and plant pathogens. For example, blight and blast are major diseases of rice plants which can decimate a crop. Some plants cannot be cultivated in certain parts of the world because of the presence of diseases in such locations to which the plants are susceptible. For example, the main diseases in potato are bacterial soft rot and bacterial wilt caused by *Erwinia carotovora* and *Pseudomonas solanacearum*, respectively. These diseases are primarily responsible for limiting the growth of potatoes in many areas of Asia, Africa, South and Central America. Moreover, pesticides are becoming increasingly difficult to use in an effective, and yet environmentally acceptable manner. Therefore, it would be desirable to have available for cultivation plants which are resistant to insects and other pathogens.

It is well known that the pupae of Hyalophora (a type of silk moth) respond to bacterial infection by the synthesis of mRNAs which culminate in the production of about 15 to 20 new proteins. Lysozyme, the antibacterial protein found in egg white and human tears, and two other classes of antibacterial peptides, called cecropins and attacins, have been purified from hyalophora humor. These proteins have a rather broad spectrum of activity in that they are effective on many different types of bacteria. Thus, the insects have evolved a rather successful and novel means to fight bacterial infections. Although a traditional immunologist would think this system lacks specificity, the insect has a rather potent arsenal of at least three different antibacterial proteins which may work in different ways to destroy bacterial pathogens. Thus, the invading bacteria is presented with a formidable challenge which is very difficult to circumvent. While a bacterial pathogen may be naturally resistant to one, it is highly improbable that it would be resistant to all three toxins. Although the exact mode of action of the protein toxins is not fully understood, they are generally procaryote specific and appear to be benign to eucaryotic insect cells.

As mentioned above, the property of certain peptides to induce lysis of procaryotic microorganisms such as bacteria is well known. For example, U.S. Pat. Nos. 4,355,104 and 4,520,016 to Hultmark et al describe the bacteriolytic properties of some cecropins against Gram-negative bacteria. Quite interestingly, the cecropins described in the Hultmark et al patents were not universally effective against all Gram-negative bacteria. For example, the cecropins described therein lysed *Serratia marcescens* D61108, but not *Serratia marcescens* D611. Moreover, cecropins have generally been reported to have no lytic activity towards eucaryotic cells such as insect cells, liver cells and sheep erythrocytes, as reported in the Hultmark patents; International Patent Publication WO/8604356; Andreu et al, *Biochemistry*, vol. 24, pp. 1683–88 (1985); Boman et al, *Developmental and Comparative Immunology*, vol. 9, pp. 551–558 (1985); and Steiner et al, *Nature*, vol. 292, pp. 246–248 (1981).

Other lytic peptides heretofore known include, for example, the sarcotoxins and lepidopterans. Such peptides generally occur naturally in the immune system of *Sarcophaga peregrina* and the silkworm, lepidopteran, respectively, as reported in Nakajima et al, *The Journal of Biological Chemistry*, vol. 262, pp. 1665–1669 (1987) and Nakai et al, *Chem. Abst.* 106:214351w (1987).

A number of the antibacterial polypeptides have been found to be useful when the genes encoding therefor are incorporated into various animals. Such transformation of animals with genes encoding therefor are described in U.S. patent application Ser. No. 069,653, filed Jul. 25, 1986, by Jesse M. Jaynes, Frederick M. Enright and Kenneth F. White, now abandoned, which is hereby incorporated herein by reference.

Polynucleotide molecules expressible in *E. coli* and having the sequence araB promoter operably linked to a gene which is heterologous to such host are also known. The heterologous gene codes for a biologically active polypeptide. A genetic construct of a first genetic sequence coding for cecropin operably linked to a second genetic sequence coding for a polypeptide which is capable of suppressing the biological effect of the resulting fusion protein towards an otherwise cecropin-sensitive bacterium is also described in International Publication WO86/04356, Jul. 31, 1986.

The Hultmark et al patents mentioned above also mention that there are no known antibodies to cecropin, indicating a wide acceptability for human and veterinary applications, including one apparently useful application for surface infections because of the high activity against pseudomonas. Similarly, EPO publication 182,278 (1986) mentions that sarcotoxins may be expected to be effective in pharmaceutical preparations and as foodstuff additives, and that antibacterial activity of sarcotoxin can be recognized in the presence of serum. Shiba, *Chem. Abstr.* 104: 230430K (1985) also mentions preparation of an injection containing 500 mg lepidopteran, 250 mg glucose and injection water to 5 ml.

Several analogs of naturally-occurring cecropins, sarcotoxins and lepidopterans have been reported. For example, it is reported in Andreu et al, *Proc. Natl. Acad. Sci. USA*, vol. 80, pp. 6475–6479 (1983) that changes in either end of the amino acid sequence of cecropin generally result in losses in bactericidal activity in varying degrees against different bacteria. It is reported in Andreu et al (1985) mentioned above that $Trp^2$ is clearly important for bactericidal activity of cecropin, and that other changes in the 4, 6 or 8 position have different effects on different bacteria. From the data given in Table II at page 1687 of Andreu et al (1985), it appears that almost any change from natural cecropin generally adversely affects its bactericidal activity. Cecropin is defined in International Publication WO86/04356 to include bactericidally active polypeptides from any insect species and analogs, homologs, mutants, isomers and derivatives thereof having bactericidal activity from 1% of the naturally-occurring polypeptides up to 100 times or higher activity of the naturally-occurring cecropin. Other references generally discuss the effects of the α-helix conformation and the amphiphilic nature of cecropin and other lytic peptides.

It is known that lysozyme and attacins also occur in insect homolymph. For example, it is reported in Okada et al, *Biochem. J.*, vol. 229, pp. 453–458 (1985) that lysozyme participates with sarcotoxin against bacteria, but that the bactericidal actions are diverse. Steiner et al mentioned above suggests that lysozyme plays no role in the antibacterial activity of insect hemolymph other than to remove debris following lysis of bacteria by cecropin. Merrifield et al, *Biochemistry*, vol. 21, pp. 5020–5031 (1982) and Andreu et al (1983) mentioned above state that cecropin purified from insect hemolymph may be contaminated with lysozyme, but demonstrate that the synthetically prepared cecropin is as bactericidally active as purified cecropin from insect hemolymph.

The treatment of eucaryotic pathogens and other cells with lytic peptides, and novel lytic peptides, is the subject matter of U.S. Ser. No. 102,175, filed Sep. 29, 1987, by Jaynes, Enright, White and Jeffers, which is hereby incorporated herein by reference.

Approximately 70% of the world's human population lives in underdeveloped countries, and have diets nutritionally inadequate in proteins, fats and calories. Malnutrition in these countries is wide-spread and persistent. Protein malnutrition can usually be attributed to a deficiency in the diet of one or more of the essential amino acids. The major food staples of many underdeveloped countries, cereals and tubers, are deficient in most limiting essential amino acids. When a major portion of the diet consists of such staples, the result is limiting essential amino acid deficiency. In children, this condition is particularly debilitating, because of the large requirement for high quality polypeptide needed for normal growth and development.

Protein malnutrition of this type could be alleviated or eliminated by adding supplements to the diet, which supplements contained polypeptides high in these limiting essential amino acids. Such polypeptides would have to be susceptible to digestion by normal human or animal proteases. Further, such polypeptides would be manufactured by cloning and expression of synthetic DNA.

Synthetic DNA of a desired sequence can now be constructed using modern chemical techniques, and the DNA can then be cloned into various microorganisms using recombinant DNA technology. It is known, for example, that a synthetic DNA which codes for poly(1-aspartyl-1-phenylalanine) can be cloned and expressed in *E. coli*. Doel et al, *Nucleic Acids Research*, Vol. 8, No. 20, pp. 4575–4592 (1980). Also Tangus et al, *Applied and Environmental Microbiology*, Vol. 43, No. 3, pp. 629–635 (March, 1982), have obtained expression of a cloned homopolymeric synthetic DNA sequence coding for poly-1-proline.

A number of United States patents have issued concerning the synthesis of polypeptides by conventional polypeptide sequencing, or by using DNA technology. Such patents include U.S. Pat. No. 3,796,631 to Choay et al, U.S. Pat. No. 3,850,749 to Kaufman et al, U.S. Pat. No. 3,299,043 to Schramm et al, U.S. Pat. No. 3,594,278 to Naylor, and U.S. Pat. No. 3,300,469 to Bernardi et al. U.S. Pat. No. 4,338,397, issued July 1982 to Gilbert et al, discloses a method for synthesizing within a bacterial host, and secreting through the membrane of the host, a selected mature protein or polypeptide using these DNA techniques. The polypeptide can be any selected polypeptide such as proinsulin, serum albumin, and the like.

Peptides high in limiting essential amino acids and transformed plants expressing the same are the subject matter of U.S. Ser. No. 837,722, filed Mar. 7, 1986, by Jaynes; and U.S. Ser. No. 837,211 filed Mar. 8, 1986 by Jaynes, both now abandoned, which are hereby incorporated herein by reference.

SUMMARY OF THE INVENTION

The present invention involves the genetic transformation of plants, including gymnosperms, dicots and monocots, to express foreign genes to enhance one or more characteristics of the plants, such as disease or pest resistance, and/or nutritional quality.

In one aspect the invention provides a plant having a heterologous gene encoding for an antimicrobial agent. The gene is preferably expressible, and the plant may be, for example, either a gymnosperm, a monocotyledon or a dicotyledon. The antimicrobial agent may be, for example, a lytic peptide such as attacin, lysozyme or cecropin, or an antiviral agent such as micRNA.

In another aspect, the invention provides a plant having a heterologous gene encoding for a polypeptide or protein comprising at least 25–60 weight percent of limiting amino acids selected from lysine, tryptophan, methionine, threonine, and isoleucine. The gene is preferably expressible, and the plant may be a monocot or a dicot. In one embodiment, the polypeptide is preferably the product of genes constructed by random synthesis of a mixture of codon pairs for the limiting essential amino acids. In another preferred embodiment, the protein is designed for stability and digestability, as well as a high proportion of limiting essential amino acids.

In another aspect of the invention, there is provided a plant having at least a first heterologous gene encoding for an antimicrobial agent, and a second heterologous gene encoding for a polypeptide or protein comprising at least 25–60 weight percent of limiting essential amino acids selected from lysine, tryptophan, methionine, threonine, and isoleucine. The plant may be a monocot or a dicot, and the genes are preferably expressible.

Another aspect of the invention is the provision of methods for genetically transforming plants with a heterologous gene coding for (a) antimicrobial agents such as, for example, cecropin and micRNA, or (b) polypeptides comprising at least 25–60 weight percent of limiting essential amino acids selected from lysine, tryptophan, methionine, threonine, and isoleucine. One such method includes the steps of incubating plant protoplasts in the presence of a vector containing the gene under conditions effective to induce uptake of the gene by the protoplasts, selecting and cloning the incubated protoplasts expressing the gene, and regenerating a whole plant from the clones to obtain a plant homozygous for expression of the gene.

Another such method includes the steps of electroporating plant protoplasts in the presence of a vector containing the gene, selecting and cloning the electroporated protoplasts expressing the gene, and regenerating a whole plant from the clones to obtain a plant homozygous for expression of the gene.

A further such method includes the steps of introducing a vector containing the gene into a plant during development of its reproductive structures, harvesting seeds produced by the plant, generating plants from the seeds, and selecting and reproducing the seed-generated plants to obtain a plant homozygous for expression of the gene.

In yet another aspect of the invention, there is provided a novel lytic peptide having the amino acid sequence αα, αβ or βα wherein α represents the amino acid sequence LXXLLXLLXXLLXL, β represents the amino acid sequence LLLLLLLLLLLSLS or the mirror image thereof so that the "SLS" end thereof is near a terminus of the peptide, and X represents K or R.

DESCRIPTION OF THE INVENTION

1. Introduction

The plant of the present invention has a heterologous gene coding for an antimicrobial polypeptide and/or a polypeptide relatively high in limiting essential amino acids. As used herein, the term "plant" generally includes trichophyta, and particularly pteropsida such as gymnosperms, monocots and dicots. Representative examples of monocots include rice, wheat, barley, rye, corn, and other grasses, bananas, palms, lilies, orchids, sedges, and the like. Representative dicots include potatoes, carrots, sweet potatoes, willows, oaks, elm, maples, apples, roses, buttercups, petunias, phlox, violets, sunflowers, and the like. Generally, the antimicrobial gene is desirable in ornamental plant species as well as species cultivated for food, fiber, wood products, tanning materials, dyes, pigments, gums, resins, latex products, fats, oils, drugs, beverages and the like. On the other hand, the gene for enhanced nutritional quality is desirably expressed in plants cultivated for food, such as, for example, grains, legumes, nuts, vegetables, fruits, spices and the like, but there is generally no advantage to having this gene expressed in non-food plants.

The plants should express the heterologous gene, and are preferably homozygous for expression thereof. Generally, the gene will be operably linked to a promoter inducible in the cells of the particular plant. The expression should be at a level such that the characteristic desired from the gene is obtained. For example, the expression of the gene for antimicrobial resistance should confer some measurable enhancement of pathogen resistance to the plant relative to the same species without the gene. Similarly, the expression of the gene for enhanced nutritional quality should result in a plant having a relatively higher content of one or more limiting essential amino acids compared to that of the same species without the gene. On the other hand, it will generally be desired to limit the excessive expression of the gene in order to avoid significantly adversely affecting the normal physiology of the plant, i.e. to the extent that cultivation thereof becomes difficult. Promotors such as CaMV 19s, CaMV 35s and the like are contemplated as being suitable in most plants.

2. Antimicrobial Agents

The antimicrobial genes in the plants of the present invention generally encode for antibacterial and/or antifungal polypeptides, and/or antiviral agents such as micRNA, not normally found in the particular plant species. Suitable antimicrobial polypeptides are, for example, derived from insect hemolymph, such as attacin. A preferred class of antimicrobial polypeptides include the lytic peptides. Exemplary lytic peptides include lysozymes, cecropins, attacins, melittins, magainins, bombinins, xenopsins, caeruleins, the polypeptide from gene 13 of phage P22, S protein from lambda phage, E protein from phage PhiX174, and the like. However, lytic peptides such as the melittins, bombinins, and magainins are generally relatively high in lytic activity, and are therefore less preferred since host plant cells may be adversely affected thereby.

As used herein, the term "lytic peptide" includes any polypeptide which lyses the membrane of a cell in an in vivo or in vitro system in which such activity can be measured. Suitable lytic peptides used in the present invention have lytic activity toward one or more plant pathogens such as fungi and bacteria. Exemplary fungal pathogens include species of Helminthosporium (e.g. late blight), Trichophyton, Colletotricium, Ceratocystis (e.g. Dutch elm disease), Fusarium, Phytophthorax, Rhigoctoria and the like. Representative examples of bacterial pathogens include species of Pseudomonas, Erwinia (e.g. fire blight), Xanthomonas, Clavibacter and the like.

Preferred lytic peptides have from about 30 to about 40 amino acids, at least a portion of which are arranged in an amphiphilic α-helical conformation having a substantially hydrophilic head with a positive charge density, a substantially hydrophobic tail, and a pair of opposed faces along the length of the helical conformation, one such face being predominantly hydrophilic and the other being predominantly hydrophobic. The head of this conformation may be taken as either the amine terminus end or the carboxy terminus end, but is preferably the amine terminus end.

Suitable lytic peptides generally include cecropins such as cecropin A, cecropin B, cecropin D, and lepidopteran; sarcotoxins such as sarcotoxin IA, sarcotoxin IB, and sarcotoxin IC; and other polypeptides such as attacin and lysozyme obtainable from the hemolymph of any insect species which have lytic activity against bacteria and fungi similar to that of the cecropins and sarcotoxins. It is also contemplated that lytic peptides may be obtained as the lytically active portion of larger peptides such as certain phage proteins such as S protein of λ phage, E protein of Phix174 phage and P13 protein of P22 phage; and C9 protein of human complement. As used herein, classes of lytically active peptides such as, for example, "cecropins," "attacins" and "phage proteins," and specific peptides within such classes, are meant to include the lytically active analogues, homologues, fragments, precursors, mutants or isomers thereof unless otherwise indicated by context. Of these exemplary lytic peptides, those having fewer than about 30 amino acids such as the melittins are generally less preferred in the present invention because of their lack of specificity for bacteria and fungi as indicated by their hemolytic potential, whereas those with more than about 40 amino acids such as attacins and lysozymes may not be sufficiently lytic when used alone to provide a broad spectrum of microbial resistance. On the other hand, those having between about 30 and about 40 amino acids, such as cecropins and sarcotoxins are generally more preferred because of their specificity for lysing pathogens over host cells.

Hydrophilic amino acids generally include and generally have the respective relative degree of hydrophobicity (at pH 7.0; kcal/mol) as follows: aspartic acid (D), -7.4; glutamic acid (E) -9.9; asparagine (N), -0.2; glutamine (Q), -0.3; lysine (K), -4.2; arginine (R), -11.2; serine (S), -0.3; and cysteine (C), -2.8. Hydrophobic amino acids generally include and generally have the respective relative degree of hydrophobicity as follows: histidine (H), 0.5; threonine (T), 0.4; tyrosine (Y), 2.3; tryptophan (W), 3.4; phenylalanine (F), 2.5; leucine (L), 1.8; isoleucine (I), 2.5; methionine (M), 1.3; valine (V), 1.5; and alanine (A), 0.5. Glycine has a relative degree of hydrophobicity of 0 and may be considered to be hydrophilic or hydrophobic.

The amino acid homology of peptides can be readily determined by contrasting the amino acid sequences thereof as is known in the art. Similarly, the amphiphilic homology of peptides can be determined by contrasting the hydrophilicity and hydrophobicity of the amino acid sequences. The amino acid sequences of some preferred lytic peptides are compared to cecropin B by tabulation and construction of Edmundson helical wheels in the aforementioned application U.S. Ser. No. 102,175, now abandoned.

Cecropin B is a potent bacteriolytic peptide which occurs naturally and can be obtained from insects as described in the Hultmark et al patents mentioned above, by direct peptide synthesis, or from genetically transformed host cells as described in the aforementioned Publication WO/086/04356. As determined by construction of a helical wheel, fourteen of the sixteen amino acids on the hydrophilic face of cecropin B are hydrophilic, while eleven of the twenty amino acids on the hydrophilic face are hydrophilic, for a total of eleven "imperfections". It is contemplated that the removal or replacement of $Gly^{23}$ and $Pro^{24}$ would result in a more lytic peptide with only six imperfections in the amphiphilic helical conformation. In addition, proline is known to disrupt the helical conformation, and its removal may permit a more helical conformation and, hence, more lytic activity. Note that the helical wheel constructs for cecropin SB-37, cecropin D and Shiva 1 are typically constructed assuming that the end region prolines would disrupt the α-helical conformation there and this can be indicated by placing proline and the preceding amino acids outside the corresponding wheel construct.

Cecropin SB-37 is an analogue which was prepared using a peptide synthesizer and is about as lytically active as cecropin B. It has 94% homology therewith in its amino acid sequence and its amphiphilicity. As seen from a helical wheel construct thereof, two of the seventeen amino acids are hydrophilic on the hydrophobic face, while eight of twenty are hydrophobic on the hydrophilic face. It is similarly contemplated that if $Gly^{23}$ and $Pro^{24}$ were removed or replaced, it would have only five imperfections in the amphiphilic conformation, and thus be more lytically active.

Similarly, the other naturally occurring lytic peptides cecropin A, cecropin D, lepidopteran, sarcotoxin 1A, sarcotoxin 1B and sarcotoxin 1C approximate the amphiphilic helical conformation of cecropin B to varying degrees. With the exception of cecropin A which is about as lytically active as cecropin B and SB-37, these peptides are generally less lytically active against bacteria than cecropin B. However, it is likewise contemplated that the lytic activity thereof may be improved by removing amino acids from the sequence thereof, for example, $Val^{19}$ and $Ile^{20}$ from cecropin D or $Gly^{23}$ and $Pro^{24}$ from lepidopteran or cecropin A.

Another peptide designated herein as "Shiva 1" was prepared using a peptide synthesizer and has the amino acid sequence MPRWRLFRRIDRVGKQIKQGILRAG-PAIALVGDARAVG. While this peptide has only a 46% amino acid homology with cecropin B, its amphiphilic homology therewith is 100%. Quite surprisingly, however, Shiva 1 is generally much more lytically active than cecropin B, and it is contemplated that its lytic activity may be further enhanced by removal or replacement of $Gly^{23}$ and $Pro^{24}$.

A cecropin SB-37 homologue designated herein as "*cecropin SB-37" is identical thereto except for the substitution of glutamic acid in the fourth position (for threonine; corresponding to the second position of cecropin B) and lysine in the eighth position (for leucine; corresponding to the sixth position in cecropin B). Substitutions in these positions may reduce the lytic activity of the cecropin SB-37 against procaryotes by as much as 90% as reported in Andreu et al (1985) mentioned above. Quite surprisingly, however, it has been found that the lytic activity of *cecropin SB-37 against many pathogens is generally comparable to cecropin SB-37.

Another preferred class of lytic peptides contemplated as being suitable for expresison in the plants of the present invention include polypeptides having the sequence αα, αβ, and βα, wherein α has the amino acid sequence LXXLLXLLXXLLXL, β has the amino acid sequence LLLLLLLLLLSLS or the mirror image thereof so that the "SLS" end thereof is near or at a terminus of the peptide, preferably the amino terminus, and each X independently represents K or R. The following polypeptides are designated herein as indicated:

| DESIGNATION | SEQUENCE | X |
|---|---|---|
| Shiva 2 | αβ | K |
| Shiva 3 | βα | K |
| Shiva 4 | αα | R |
| Shiva 5 | αα | K |
| Shiva 6 | αβ | R |
| Shiva 7 | βα | R |

Of these, Shiva 3, Shiva 4 and Shiva 7 may be too lytically active to be used in plants at high expression levels, and might need to be employed at relatively low expression levels. However, all of these Shiva polypeptides are contemplated as having general utility as lytic peptides separate and apart from expression in the plants of this invention, e.g. in inducing lysis of cells in vitro.

The amino acid sequences of the foregoing exemplary lytic peptides as well as other lytic peptides contemplated for use in the plant transformants in the present invention are listed in Table I.

TABLE I

| Peptide | | Amino Acid Seguence |
|---|---|---|
| CECROPIN A | | KWKLFKKIEKVGQNIRDGIIKAGPAVAVVGQATQIAK |
| CECROPIN B | | KWKVFKKIEKMGRNIRNGIVKAGPAIAVLGEAKALG |
| CECROPIN D | | WNPFKELEKVGQRVRDAVISAGPAVATVANATALAK |
| LEPIDOPTERAN | | RWKIFKKIEKMGRNIRDGIVKAGPAIEVLGSAKALG |
| SARCOTOXIN IA | | GWLKKIGKKIERVGQHTRDATIQGLGIAQQAANVAATAR |
| SARCOTOXIN IB | | GWLKKIGKKIERVGQHTRDATIQVIGVAQQAANVAATAR |
| SARCOTOXIN IC | | GWLRKIGKKIERVGQHTRDATIQVLGIAQQAANVAATAR |
| SB-37 | MP | KWKVFKKIEKVGRNIRNGIVKAGPAIAVLGEAKALG |
| MOD. SB-37 | MP | KEKVFLKIEKMGRNIRNGIVKAGPAIAVLGEARALG |
| SHIVA-1 | MP | RWRLERRIDRVGKQIKQGILRAGPAIAVLGDARAVG |
| MOD. SHIVA- | MP | RERLFLRIDRVGKQIKQGILRAGPAIALVGDARAVG |
| SHIVA-2 | | LKKLLKLLKKLLKLLLLLLLLLLLSLS |
| SHIVA-3 | | SLSLLLLLLLLLLLLKKLLKLLKKLLKL |
| SHIVA-4 | | LRRLLRLLRRLLRLLRRLLRLLRRLLRL |
| SHIVA-5 | | LKKLLKLLKKLLKLLKKLLKLLKKLLKL |
| SHIVA-6 | | LRRLLRLLRRLLRLLLLLLLLLLLLSLS |
| SHIVA- 7 | | SLSLLLLLLLLLLLRRLLRLLRRLLRL |
| MELITTIN | | GIGAVLKVLTTGLPALISWIKKKRQQ |
| MI MELITTIN | | QQRKRKIWSILAPLGTTLVKLVAGIG |
| ART. MELITTIN | | LLQSLLSLLQSLLSLLLQWLKRKRQQ |
| MAGAININ 1 (PGS) | | GIGKFLHSAGKFGKAFVGEIMKS |
| PGS | | GIGKFLHSAKKFGKAFVGEIMNS |
| MAGAININ 2 (PGS) | | GIGKFLHSAKKFGKAFVGEIMNS |
| BOMBININ | | GIGALSAKGALKGLAKGLAZHFAD |
| XENOPSIN PF | | GWASKIGQTLGKIAKVGLKELIGPK |
| CAERULEIN PF | | GFGSFLGKALKAALKIGANALGGSPQQ |
| PGL | | GMASKAGAISGKIAKVALKAL |
| DEGRADO ACT. | | LKKLLKLLKKLLKLLKKLLKLLKKLLKL |
| C9 INC. | | KMKNAHLKKQNLERAIEDYINEFSVRR |
| λS PROTEIN INC. | | MKMPEKHDLLAAILAAKEQGIGAILAFAMAYLRGR |
| P22 13 PRO. INC. | | MKKMPEKHDLLTAMMAAKEQGIGAILAFAMAYLRGR |
| φX174 INC. | | MVRWTLWDTLAFLLLSLLLPSLLIMFIPSFKRPVS |

The DNA sequences coding for the foregoing peptides can be readily determined and synthesized according to established principles and techniques in the art.

Also included within the scope of the term "antimicrobial agents" as used herein are antiviral agents, inclusive of micRNA or antisense RNA for viruses and viroids replicatable in plants. Exemplary viruses infectious in plants include tobacco mosaic virus, tobacco ringspot virus, potato leaf-roll virus, potato viruses X and Y and the like. Representative examples of viroids replicatable in plants include potato spindle tuber viroid, cadang-cadang viroid, avocado sun blotch viroid, and the like. Antisense RNA, or micRNA as it is sometimes called, generally inhibits or blocks translation of viruses and viroids so that replication thereof in infected plant cells is inhibited or prevented. Such micRNA is preferably complementary to the micRNA (or DNA in the case of RNA viruses) of the virus replication gene, and such complementarity and concomitant hybridization prevents translation or transcription thereof. In the case of viroids, a single micRNA appears to be sufficient for protection against all known viroids because of a common DNA sequence in their central conserved regions. For prophylaxis against viruses, on the other hand, several micRNA's may be required to block a wide spectrum of viruses.

An exemplary genetic sequence for a micRNA complementary to the tobacco mosaic virus is as follows:

```
5' GATCTCCACGGTTGTGGCCATATAAT-
    CATCGTGTTTTTCAA 3'
```

Exemplary contemplated genetic sequences for micRNA's complementary to the African cassava mosaic virus are as follows:

```
ACMV1: 5' AGGGGCCAACCGTA 3'
ACMC2: 5' GCCCCGGTTGGCAT 3'.
```

Viroid antisense RNA's are coded by the following exemplary DNA sequences:

```
PSTV1: 5' GATCTAGGGATCCCCGGGGAAACCT 3'
PSTV2: 5' GATCTAGGTTTCCCCGGGGATCCCT 3'.
```

3. Polypeptides High in Limiting Essential Amino Acids

A predominant limiting factor in animal and human nutrition is protein quality. Certain proteins, such as egg protein, are considered to be of very high quality because they contain disproportionately high levels of limiting essential amino acids. Limiting essential amino acids are those which are found in very restricted quantities in most proteins, and which, when ingested by an organism, limit the amount of protein which that organism can produce. The five most limiting essential amino acids are lysine, methionine, tryptophan, threonine and isoleucine. Of the total protein in egg, 22.8% consists of these limiting amino acids. The average cereal grain protein (rice, corn, wheat, barley) is composed of about 13% of these five most limiting essential amino acids. The following Tables list these five limiting amino acids in the cereal grains and in roots and tubers.

TABLE II

AMINO ACID RANK FOR A CHILD'S DIET OF A CALORIC AMOUNT OF CEREAL GRAIN

| | Amino Acid | | | | |
|---|---|---|---|---|---|
| Cereal | Isoleucine | Lysine | Methionine | Threonine | Tryptophan |
| Barley | 1 | 1 | 2 | | |
| Corn | | 1 | | 3 | 2 |
| Rice | 1 | 1 | 4 | 3 | 2 |
| Wheat | 2 | 1 | | 3 | |

TABLE III

AMINO ACID RANK FOR A CHILD'S DIET OF A CALORIC AMOUNT OF ROOT OR TUBER

| | Amino Acid | | | | |
|---|---|---|---|---|---|
| | Isoleucine | Lysine | Methionine | Threonine | Tryptophan |
| Cassava | 3 | 4 | 1 | 2 | 2 |
| Potato | 4 | 5 | 2 | 3 | 1 |
| Sweet Potato | 3 | 3 | 2 | 3 | 1 |

It will be seen that generally lysine is the first limiting amino acid in a cereal and tryptophan is the first limiting amino acid in a root or tuber diet for a human child. However, even if the lysine or tyrptophan requirement is met, then the other amino acids become limiting depending upon which of these foods is being consumed. In the case of legumes, the first limiting amino acid would be methionine.

The present embodiment provides an ideal polypeptide for use in supplementing the diets of animals and humans to meet their daily limiting essential amino acid requirement. The polypeptide of the present embodiment is particularly suitable for supplementing diets which consist largely of cereals, roots, tubers and legumes. Thus, the present invention provides a polypeptide which has elevated levels as compared to proteins known in the art, of lysine, methionine, tryptophan, threonine and isoleucine. In this broadest embodiment, the polypeptides of this invention will contain from 25–60 weight percent of these limiting essential amino acids. The polypeptide preferably contains at least two of these limiting essential amino acids, more preferably at least three, and especially four or all five.

For purposes of this embodiment of the invention, a protein will be defined as an amino acid chain containing more than 50 amino acids. A polypeptide will be an amino acid chain having less than 50 amino acids.

According to this embodiment, the cloning and expression of synthetic DNA containing repeated selected codons for limiting essential amino acids are used as a means for improving the amino acid profiles of single cell proteins. Thus, using these techniques, single cell production of polypeptides composed largely of limiting essential amino acids are used to supplement cereal, root, tuber and/or legume diets and feed grain rations and other foodstuffs. Such supplemented foodstuffs would include any suitable foodstuff, particularly legumes, roots, tubers and cereal grains. Thus, in this embodiment is provided the synthesis, cloning and expression of genes which code for polypeptides specifically designed for their digestibility by animal proteases. These genes code for polypeptides high in limiting essential amino acids, particularly for the five most limiting amino acids of the root, tuber and cereal diet: lysine, methionine, tryptophan, threonine and isoleucine.

To determine the efficacy of some of the genes of this embodiment, they were tested with positive results, for their functional activity in a microbe such as $E.\ coli$. The test method used generally involves isolating a plasmid from a microbe such as $E.\ coli$. The plasmid may be isolated by any desired procedure, but preferably a cleared lysate procedure is employed. Next, the plasmid is digested with restriction enzyme such as, for example, EcoR1 to yield a linear molecule with an interrupted chloramphenicol resistance gene at the 72nd amino acid of the chloramphenicol-acetyl transferase (CAT) protein. In this manner, when a DNA segment is cloned into the site on the promoter, the plasmid no longer produces an active CAT protein and any recombinant clone is rendered chloramphenicol sensitive. These genes, when fused to an active bacterial plasmid promoter region, such as chloramphenicol-acetyl transferase (CAT), incorporated $^{14}C$ lysine at a rate of two to seven times that of a control during the polypeptide production cycle of the bacteria. Thus, in the present embodiment, a series of genes that encode for high quality polypeptides are designed and synthesized and the genes are expressed in a microbe.

Synthesis of the genes may be by random ligation of mixtures of small oligodeoxynucleotides. Thus, the products of ligation are heterogenous with respect to molecular weight. However, the addition of a dodecomeric linker, which contains the enzyme recognition sequence for the restriction endonuclease such as EcoR1 is at a concentration which should yield, upon digestion with EcoR1, fragments of a mean size of about 400 base pairs (bp). Suitable recombinant *E. coli.* strains are then selected for further characterization and designated. In the process of this invention, the designations given were SP44 and SP47. These designated strains contain nucleotide fragments cleaved by EcoR1 of approximately 100 bp and 300 bp, respectively.

Polypeptide synthesis is determined by the relative uptake of labeled amino acids by the recombinant *E. coli.* strains as compared to controls. The polypeptide sequences produced can be derived from the known nucleotide sequences of the DNA.

In the following Table IV, the amino acid profiles obtained in the synthetic polypeptides just described are compared with those in lactalbumin and zein.

TABLE IV

|     | Sp44(1) | Sp44(2) | Sp47(1) | Sp47(2) | Lactalbumin | Zein |
|-----|---------|---------|---------|---------|-------------|------|
| Ile | 13.1    | 0       | 6.3     | 3.1     | 6.2         | 4.2  |
| Lys | 13.3    | 20.0    | 23.0    | 16.7    | 9.0         | 0    |
| Met | 6.6     | 9.9     | 11.5    | 8.3     | 2.3         | 0    |
| Thr | 13.3    | 0       | 6.3     | 3.1     | 5.2         | 2.4  |
| Trp | 6.6     | 9.9     | 11.5    | 8.3     | 2.2         | 0    |
| Total | 53.1  | 39.8    | 58.6    | 39.5    | 24.9        | 6.6  |

Lactalbumin is a high quality milk protein, and zein is a poor quality major protein in maize. It will be seen from Table IV that proper supplementation of zein with SP44(1) or (2) or SP47(1) or (2), would markedly improve the balance of the five most limiting amino acids. The method of gene synthesis, according to this embodiment, is flexible enough to produce amino acid profiles which would be specifically designed to supplement the material to be enhanced, in this case, maize. It should be pointed out that the insertion of lysine (or arginine) at frequent intervals in these polypeptides, preferably on the average of every fifth to tenth amino acid, will provide numerous sites for proteolytic attack by trypsin.

It will be seen, therefore, that the present embodiment provides polypeptides which contain appropriate amino acids to provide a high quality product and also to be in a form which will be used to supplement foodstuffs having low quality proteins. In the broadest embodiment, the polypeptides may be described as being composed largely of the amino acids lysine, methionine, tryptophan, threonine, and isoleucine, which amino acids constitute 25–60 weight percent of the polypeptide.

In a further embodiment, a protein of the present invention has the following amino acid sequence:

GDRKKWMDRHPFLHPFLTIPFLKKWMKKWM

TIHPFLHPFLHPFLTIKKWMKKWMKKWMHPF

LKKWMKKWMKKWMTIDRKKWMTIHPFLTIP

In a still further embodiment of the invention, a smaller polypeptide which has somewhat lower quality than the foregoing large protein has the following amino acid sequence:

GTITIHPFLKKWMTIHPFLKKWMTIHPFLP

The importance of the use of the genes of the present invention may be understood from the following Table V, which sets forth the percentage of limiting essential amino acids in a number of food proteins, and compares those percentages with the supplementary polypeptide of this invention.

TABLE V

|            | Isoleucine | Lysine | Methionine | Threonine | Tryptophan | Total |
|------------|------------|--------|------------|-----------|------------|-------|
| Casein     | 6.55       | 8.01   | 3.08       | 4.23      | 1.34       | 23.21 |
| Lactalbumin| 6.21       | 9.06   | 2.25       | 5.24      | 2.20       | 24.96 |
| Whole Egg  | 6.64       | 6.40   | 3.13       | 4.98      | 1.65       | 22.80 |
| Beef       | 5.23       | 8.73   | 2.48       | 4.41      | 1.17       | 22.03 |
| Soybean    | 5.89       | 6.92   | 1.47       | 4.31      | 1.51       | 20.09 |
| Barley     | 4.26       | 3.38   | 1.44       | 3.38      | 1.25       | 13.71 |
| Corn       | 4.62       | 2.88   | 1.86       | 3.98      | .61        | 13.95 |
| Rice       | 4.40       | 3.20   | 1.80       | 3.50      | .10        | 13.00 |
| Wheat      | 4.34       | 2.74   | 1.53       | 2.88      | 1.24       | 12.72 |
| Synthetic* Protein | 8.10 | 21.60 | 16.20    | 10.80     | 10.80      | 67.50 |

These numbers represent the calculated theoretical average based on the experimental protocol used.

It may be seen from the above table, that the total of these limiting essential amino acids in the synthetic protein is 67.5 as compared to the other food proteins which range from 12.72 to 24.96. This is a remarkable increase in the amount of these limiting essential amino acids in a polypeptide since the foodstuffs with which it is compared are generally of high nutritional value.

A particularly preferred embodiment is a protein which is relatively more stable due to alternating charges in the amino acid side chains which are adjacent to each other in α-helical conformations of the protein, and which contains few, and preferably no α-helix disrupters, such as proline. Such proteins are contemplated as having a greater utility since they would be more stable, i.e., less subject to proteolytic attack by the plant enzymes, and expressible in a wider variety of plants. An exemplary protein with such characteristics, and also with approximately 20 percent of its amino acids being randomly inserted lysine, has the amino acid sequence as follows:

MFKWMKEIWKVLKDMIDKMKTFIDTLFEM

ITKLFTEVEKWMKEIWKVLKDMIDKMKTFVDTLFEM

LEMITKWFTEVEKWMKEIWKVLKDMIDKM

The DNA sequences coding for the foregoing peptides can also be readily determined and synthesized according to established principles and techniques in the art, e.g. synthesis of the oligonucleotide, or portions thereof followed by ligation.

4. Transformation of Plants

The plants of the present invention may be obtained by any of several methods. Such methods generally include direct gene transfer, chemically-induced gene transfer, electroporation, microinjection, Agrobacterium-mediated gene transfer, and the like. Some methods, such as Agrobacterium-mediated gene transfer, are generally only suitable for certain types of plants, e.g. dicots, while the other methods can generally be used to transform monocots and gymnosperms as well.

One method for obtaining the present plants is direct gene transfer in which plant cells are cultured or otherwise grown in the presence of DNA oligonucleotides containing the gene desired to be introduced into the plant. The donor DNA source is typically a plasmid or other suitable vector containing the desired gene. For convenience, reference is made below to plasmids, with the understanding that other suitable vectors containing the desired gene are also contemplated.

Any suitable plant tissue which takes up the plasmid may be treated by direct gene transfer. Such plant tissue includes, for example, reproductive structures at an early stage of development, particularly prior to meiosis, and especially 1–2 weeks pre-meiosis. Generally, the pre-meiotic reproductive organs are bathed in plasmid solution, such as, for example, by injecting plasmid solution directly into the plant at or near the reproductive organs. The plants are then self-pollinated, or cross-pollinated with pollen from another plant treated in the same manner. The plasmid solution typically contains about 10–50 µg DNA in about 0.1–10 ml per floral structure, but more or less than this may be used depending on the size of the particular floral structure. The solvent is typically sterile water, saline, or buffered saline, or a conventional plant medium. If desired, the plasmid solution may also contain agents to chemically induce or enhance plasmid uptake, such as, for example, PEG, $Ca^{2+}$ or the like.

Following exposure of the reproductive organs to the plasmid, the floral structure is grown to maturity and the seeds are harvested. Depending on the plasmid marker, selection of the transformed plants with the marker gene is made by germination or growth of the plants in a marker-sensitive, or preferably a marker-resistant medium. For example, seeds obtained from plants treated with plasmids having the kanamycin resistance gene can be identified to have taken up the plasmid by germinating the seeds in kanamycin. Plants expressing the kanamycin resistance gene will remain green, whereas those without this marker gene are albino. Presence of the desired gene transcription of mRNA therefrom and expression of the peptide can further be demonstrated by conventional Southern, northern, and western blotting techniques.

In another method, plant protoplasts are treated to induce uptake of the plasmid. Protoplast preparation is well-known in the art and typically involves digestion of plant cells with cellulase and other enzymes for a sufficient period of time to remove the cell wall. Typically, the protoplasts are separated from the digestion misture by seiving and washing. The protoplasts are then suspended in an appropriate medium, such as, for example, medium F, CC medium, etc., typically at $10^4$–$10^7$ cells/ml. To this suspension is then added the plasmid solution described above and an inducer such as polyethylene glycol, $Ca^{2+}$, Sendai virus or the like. Alternatively, the plasmids may be encapsulated in liposomes. The solution of plasmids and protoplasts are then incubated for a suitable period of time, typically about 1 hour at about 25° C. In some instances, it may be desirable to heat shock the mixture by briefly heating to about 45° C., e.g. for 2–5 minutes, and rapidly cooling to the incubation temperature. The treated protoplasts are then cloned and selected for expression of the desired gene, e.g. by expression of the marker gene and conventional blotting techniques. Whole plants are then regenerated from the clones in a conventional manner.

The electroporation technique is similar except that electrical current is typically applied to the mixture of naked plasmids and protoplasts, in an electroporation chamber in the absence or presence of polyethylene glycol, $Ca^{2+}$ or the like. Typical electroporation includes 1–10 pulses of 40–10, 000 DC volts for a duration of 1–2000 µs with typically 0.2 second intervals between pulses. Alternating current pulses of similar severity can also be used. More typically, a charged capacitor is discharged across the electroporation chamber containing the plasmid protoplast suspension.

Another method suitable for transforming dicots involves the use of Agrobacterium. In this method, Agrobacterium containing the plasmid with the desired gene is used to infect plant cells and insert the plasmid into the genome of the cells. The cells expressing the desired gene are then selected and cloned as described above. For example, one method for introduction of a foreign gene into a dicot, e.g., a tuber, root or legume, by means of a plasmid, e.g. an Ri plasmid and an Agrogacterium, e.g. *A. rhizogenes* or *A. tumefaciens*, is to utilize a small recombinant plasmid suitable for cloning in *Escherichia coli*, into which a fragment of T-DNA has been spliced. This recombinant plasmid is cleaved open at a site within the T-DNA. A piece of "passenger" DNA is spliced into this opening. The passenger DNA consists of the gene of this invention which is to be incorporated into the plant DNA as well as a selectable marker, e.g., a gene for resistance to an antibiotic. This plasmid is then recloned into a larger plasmid and then introduced into an Agrobacterium strain carrying an unmodified Ri plasmid. During growth of the bacteria, a rare double-recombination will sometimes take place resulting in bacteria whose T-DNA harbors an insert: the passenger DNA. Such bacteria are identified and selected by their survival on media containing the antibiotic. These bacteria are used to insert their T-DNA (modified with passenger DNA) into a plant genome. This procedure utilizing *A. rhizogenes* or *A. tumefaciens* gives rise to transformed plant cells that can be regenerated into intact healthy, fertile plants.

The invention is illustrated by way of the examples which follow.

DESCRIPTION OF THE PREFERRED EMBODIMENTS

EXAMPLE 1

Figure 1:
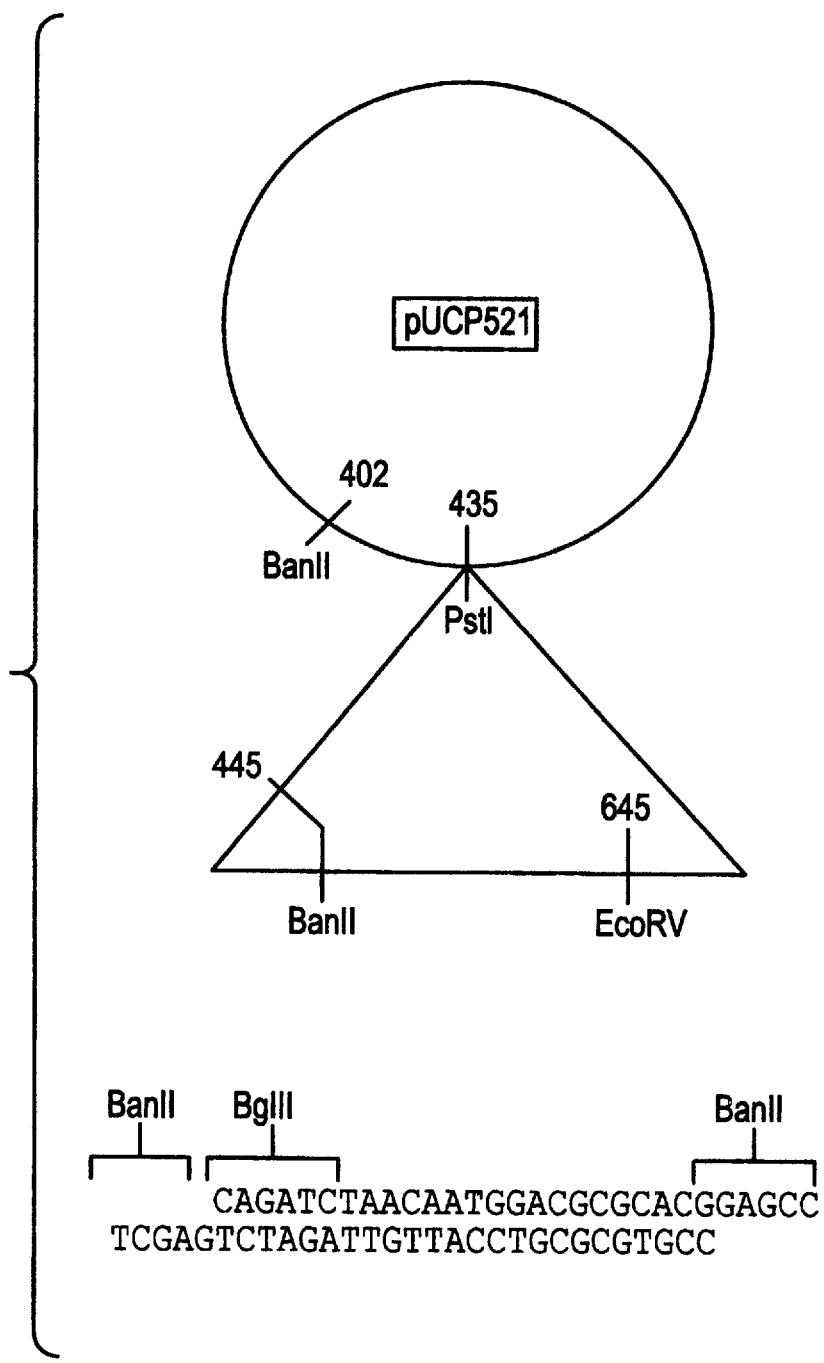
FIG. 1 is a restriction map of pUCP521 and also illustrates a DNA sequence with which a BanII fragment of pUCP521 can be ligated.

A plasmid containing an attacin cDNA sequence, the CaMV 35s promoter and kanamycin/streptomycin/spectinomycin resistance genes was constructed, and is designated herein as pMONAATT. The plasmid pCP521 was obtained from K. Xanthopoulous, and it has a 723 bp insert in the PstI site of pBR322 containing the acidic attacin cDNA sequence without methionine. pCP521 was treated with BanII and PstI to remove the attacin gene. The attacin gene was subcloned into the PstI site of pUC19 by filling in the 3' end of the attacin with T4 DNA polymerase and ligating with T4 DNA ligase. The resulting plasmid was selected for clockwise orientation and designated pUCP521. A restriction map of pUCP521 is seen in FIG. 1. This was digested with BanII. The larger fragments were isolated by gel permeation and ligated with the DNA sequence:

5' CAGATGTAACAATGGACGCGCACGGAGCC 3'
3' TCGAGTCTACATTGTTACCTGCGCGTGCC 5'

Figure 6:
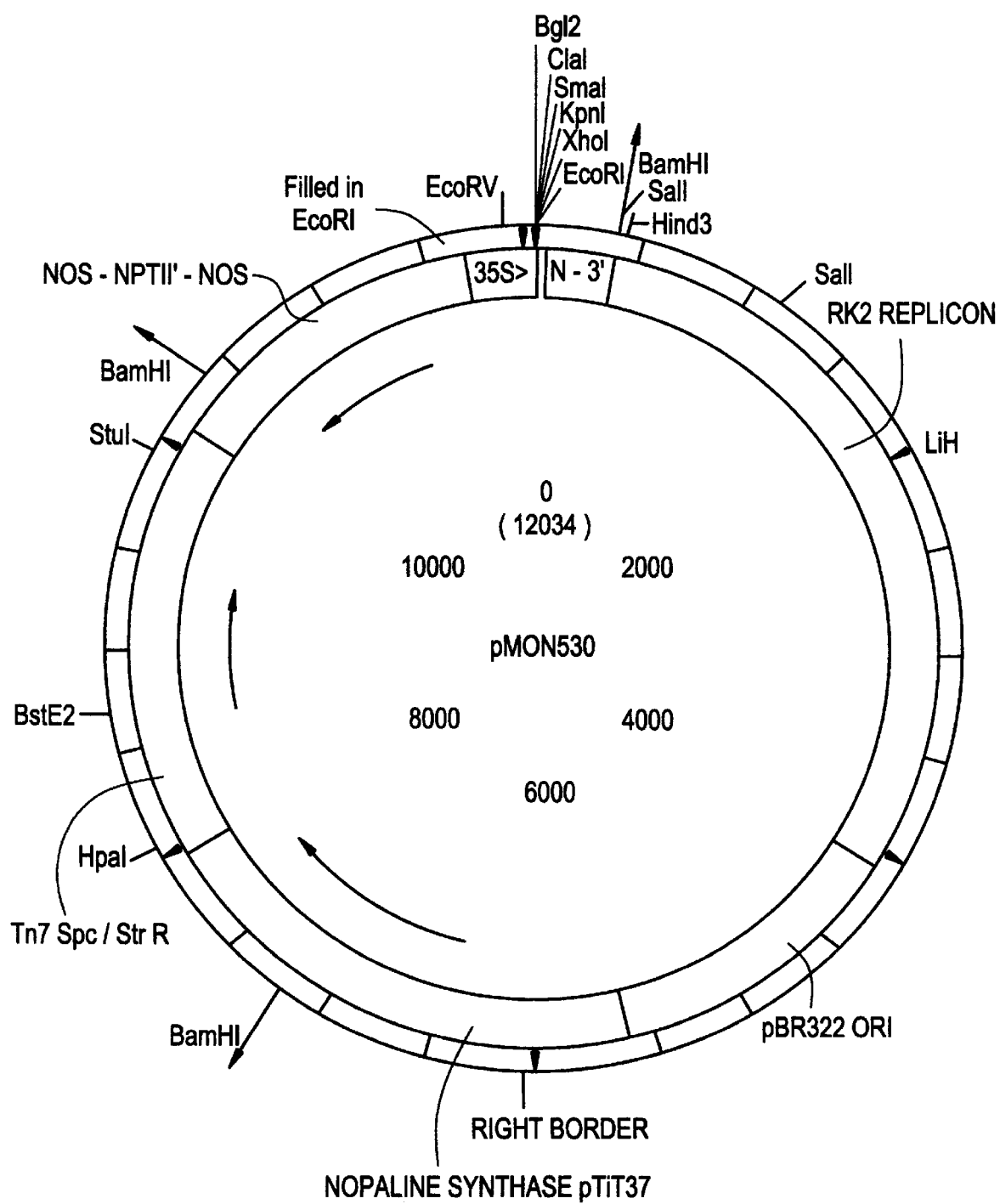
FIG. 6 is a restriction map of PMON530.
Figure 7:
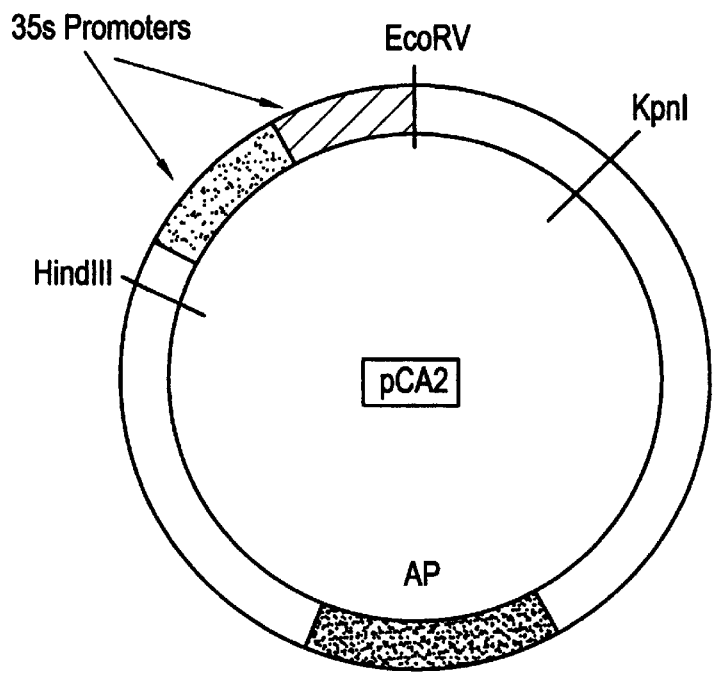
FIG. 7 is a restriction map of pCA2.

A 657 bp fragment was rescued by digestion with BglII and EcoRV. This fragment was then ligated between the BglII and SmaI sites of pMON530 and the resulting plasmid was designated pMONATT. A restriction map of unmodified pMON530 is illustrated in FIG. 6.

The plasmid pMONAATT was then placed in competent E. coli cells. Into 100 μl of cells at $10^6$ cells/ml, was added 1 μg of pMONAATT in 10 μl sterile water and 100 μl 0.01M $CaCl_2$ buffer. This mixture was incubated at 4° C. for 45 minutes, heat shocked at 42° C. for two minutes, placed in 1.5 ml Luria broth at 37° C. for two hours and plated on LB-Agar containing 50 μg/ml kanamycin sulfate. After incubation at 37° C. overnight, colonies were selected, grown and screened for kanamycin resistance and the correct attacin gene. Suitable clones in mid to late-log phase were suspended at $10^6$/ml and 0.1 ml was placed on LB-agar plates with a like amount of disarmed vector A. tumefaciens. After about 6 hours at room temperature, the plates were scraped, the cells were serially diluted several times at 1:10 dilution and replated on LB-agar containing 25 μg/ml chloramphenicol, 50 μg/ml kanamycin sulfate, and 100 μg/ml each of streptomycin and spectinomycin. Surviving A. tumefaciens were diluted 1:10 in PBS and N. tabacum leaf discs were briefly dipped in this solution and subsequently plated. After two days of incubation, cefotoxin and kanamycin were added to the media. All cells died, indicating that no transformants were obtained.

Figure 8:
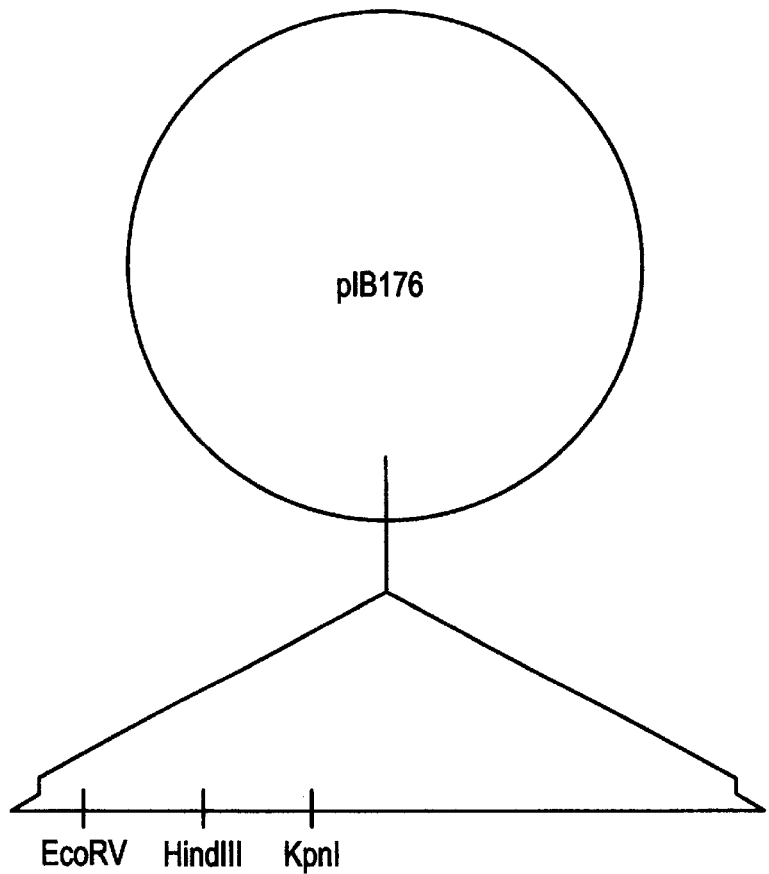
FIG. 8 is a partial restriction map of pIBI76.
Figure 9:
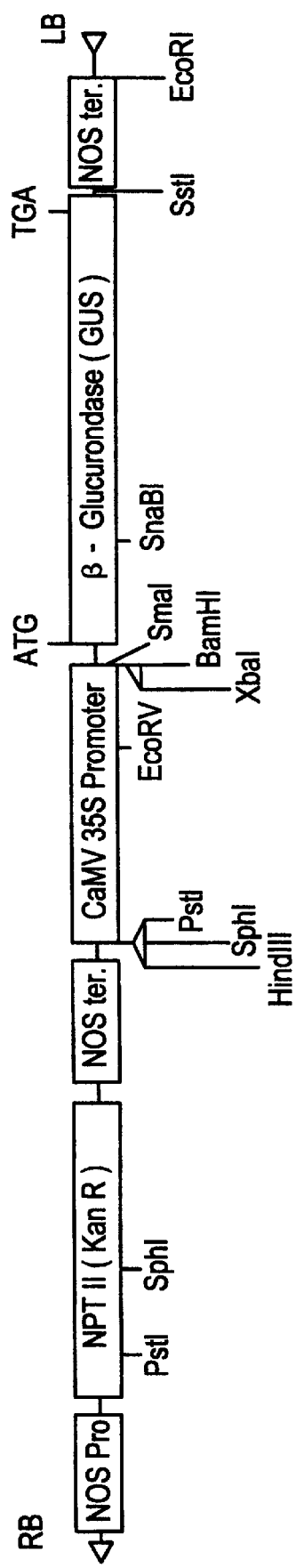
FIG. 9 is a partial restriction map of pBI121.
Figure 10:
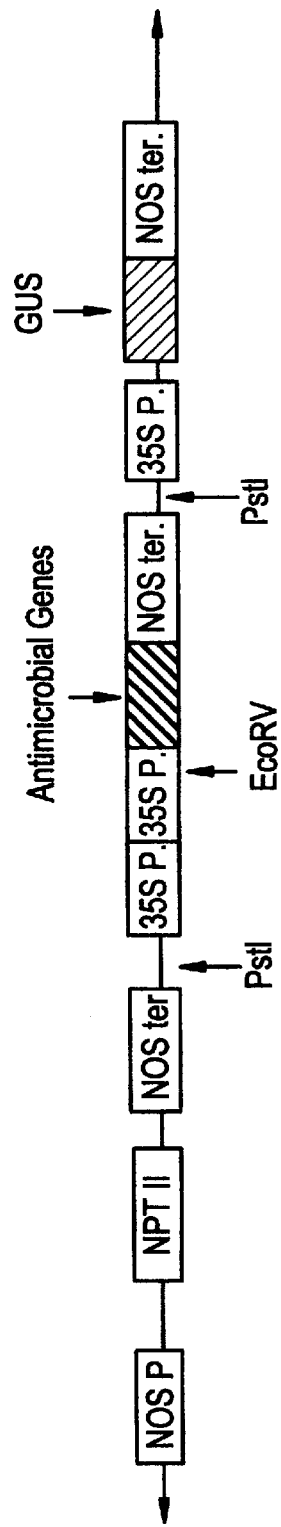
FIG. 10 is a partial restriction map of pCAMV2X.

The pMONAATT clones are digested with EcoRV and HindIII and the attacin fragment is rescued and purified from agarose gel. This fragment is subcloned into pIBI76 (FIG. 8) between the EcoRV and HindIII cleavage sites thereof. The resulting plasmid is then digested with EcoRV and KpnI and the fragment containing the attacin gene is recovered. This fragment is then subcloned into pCA2 (FIG. 12; Science, vol. 236, pp. 1299–1301 (1987)) between the EcoRV and KpnI sites. This plasmid is then digested with HindIII and PstI to rescue a fragment containing the attacin gene and duplicated CaMV 35s promoters. This fragment is then ligated into pBI121 (FIG. 9; obtained commercially from Clontech Laboratories, Inc.) between the HindIII and PstI sites to obtain the vector illustrated in FIG. 10 and designated pCAMV2X. This vector has the attacin gene under the control of the double CaMV 35s promoters, as well as a β-glucoronidase ("GUS") gene. This vector is then cloned in E. coli as described above for pMONATT. The transformed E. coli are conjugated with disarmed vector A. tumefaciens which are subsequently used to infect the tobacco leaf discs as described above. After about 2 weeks, callus tissue develops. Plants are regenerated from the callus and expression of attacin is demonstrable by blotting techniques. The plants are exposed to Pseudomonas syringae but are not infected, in contrast to untransformed plants of the same species identically exposed to the P. syringae under the same conditions.

EXAMPLE 2

Figure 2:
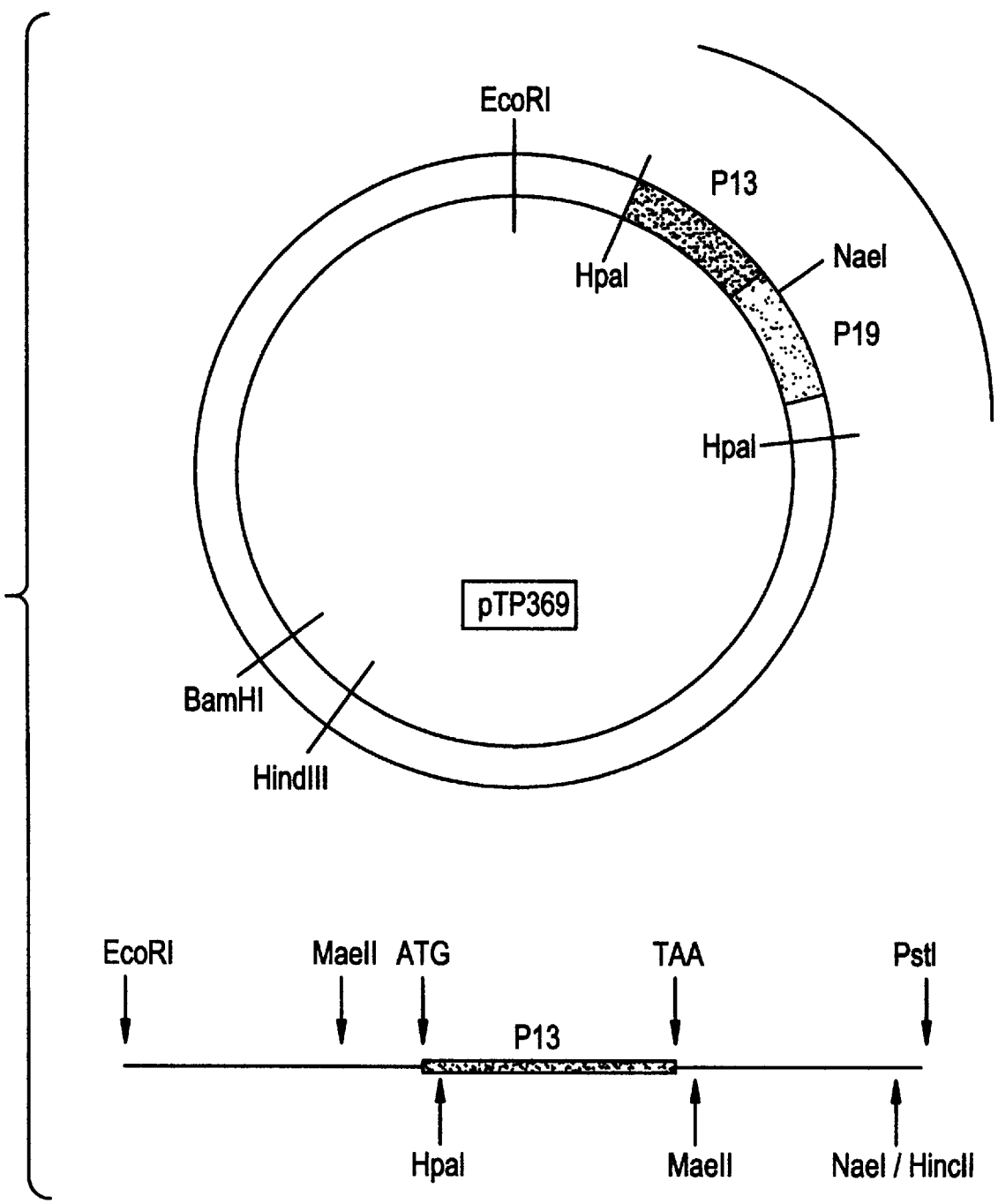
FIG. 2 is a restriction map of pTP369 of Example 2 containing the gene for protein 13 of phage 22.

A plasmid containing P13 protein of phage P22, the CAMV 35s promoter and kanamycin/streptomycin/spectinomycin resistance genes was constructed, and is designated herein as pMONP22P13. The plasmid pTP369 (FIG. 2) was obtained from A. Poteete. pTP369 was digested with EcoRI and NaeI to obtain a fragment of about 1100 bp containing the P13 protein codons. This fragment was ligated into pUC19 between the EcoRI and the HincII cleavage sites thereof to obtain a plasmid designated pTPEN1041. pTPEN1041 was digested with EcoRI and PstI, and a fragment of about 1100 bp was isolated. This was then digested with MaeII and yielded fragments of 437, 348 and 259 bp. The 437 bp fragment ends were filled in using Klenow enzyme and purified from agarose gel. This was then ligated into pMON530 between the SmaI and LiH sites, and the orientation was checked with HpaI. The resulting plasmid was designated pMONP22P13. The plasmid pMONP22P13 was cloned in E. coli and conjugated with A. tumefaciens which was then cultured with tobacco leaf discs as described in Example 1, but no transformed cells were obtained.

The P22 protein gene from the pMONP22P13 clones are then inserted in the HindIII site of pBI121 as described in Example 1, and then used in an A. tumefaciens vector to transform tobacco leaf discs. Callus eventually develops, and plants regenerated therefrom express the phage protein and are resistant to P. syringae.

EXAMPLE 3

Figure 3:
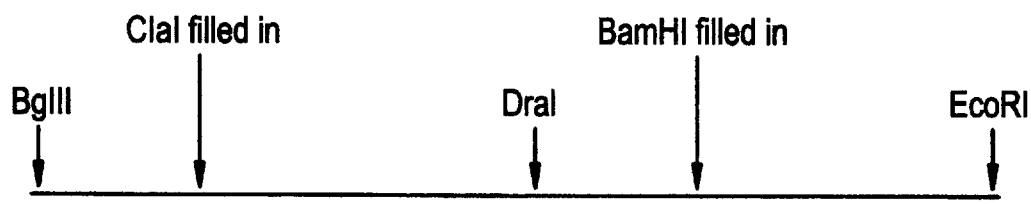
FIG. 3 is a partial restruction map of pMONP22Ly of Example 3 containing the lysozyme gene of phage P22.

A plasmid corresponding to the partial restriction map shown in FIG. 3 was constructed and designated pMONP22Ly. The plasmid pDR116 was obtained from A. Poteete and contained a fragment of about 590 bp between HindI and TaqI sites [as a BamHI-ClaI insert in a pBR322 derivative containing a BamHI in the PvuI cleavage site.] pDR116 was digested with BamHI and ClaI and the ends of the fragment containing the phage lysozyme gene was filled in using Klenow enzyme and isolated from agarose gel. This approximately 590 bp fragment was ligated into pMON530 at the SmaI/LiH site and the orientation was checked by digestion with EcoRI and DraI. The resulting plasmid was designated pMONP22Ly, cloned in E. coli and conjugated with A. tumefaciens which was then cultured with tobacco leaf discs as described in Example 1. Again, no tobacco transformants resistant to kanamycin were obtained.

The P22 lysozyme is then rescued from pMONP22Ly and inserted into pBI121 which is then used to transform E. coli, which in turn is conjugated with A. tumefaciens and used to infect tobacco leaf discs as described in Example 1. Callus eventually develops, and plants regenerated therefrom express the phage lysozyme gene and are resistant to P. syringae.

EXAMPLE 4

Figure 4:
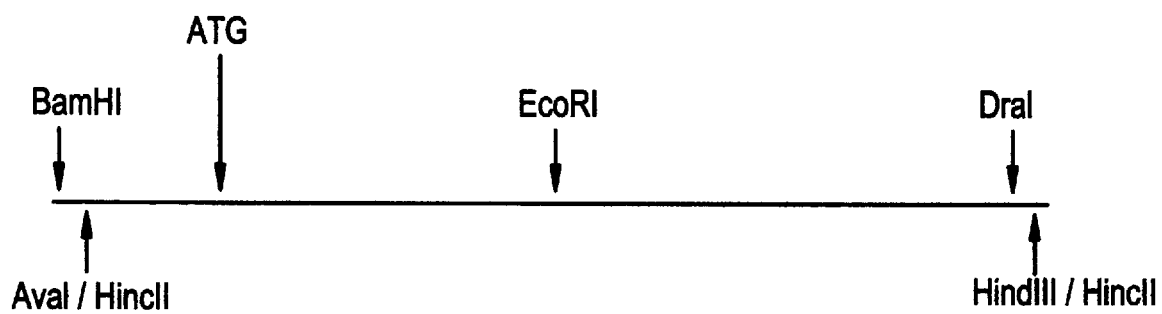
FIG. 4 is a partial restriction map of pMONT4Ly of Example 4 containing the lysozyme gene of phage T4.

A plasmid designated pMONT4Ly was constructed corresponding to the partial restriction map seen in FIG. 4. pDR105 was obtained from A. Poteete and has the lysozyme gene from phage T4 as an approximately 685 bp fragment between the AvaII and HindIII restriction sites. pDR105 was digested with AvaII and HindIII, and the lysozyme fragment was filled in with Klenow enzyme and purified from the gel. This fragment was then ligated into pUC19 between the HincII and LiH sites and designated pUCT4Ly. The orientation was checked by digestion with EcoRI, and all 18 clones had obtained clockwise rotation. pUCT4Ly was digested with BamHI, DraI and AvaII to avoid fragments of similar length to the BamHI-DraI fragment. The 646 bp BamHI-DraI fragment was ligated into pMON530 between the BglII and SmaI sites adjacent to the LiH region, and the resulting plasmid was designated pMONT4Ly. The proper orientation was confirmed with EcoRI which gave a 353 bp band, and HpaI and EcoRV which gave bands of approximately 8000, 4000 and 604 bp. pMONT4Ly was cloned in E. coli and conjugated with A. tumefaciens which was then cultured with tobacco leaf discs as described in Example 1, but again no transformats were obtained.

As in Example 1, the leaf disc infection procedure is repeated using the lysozyme gene cut from pMONT4Ly and placed in pBI121. Callus eventually develops, and plants regenerated therefrom express the T4 phage lysozyme and are resistant to P. syringae.

EXAMPLE 5

Figure 5A:
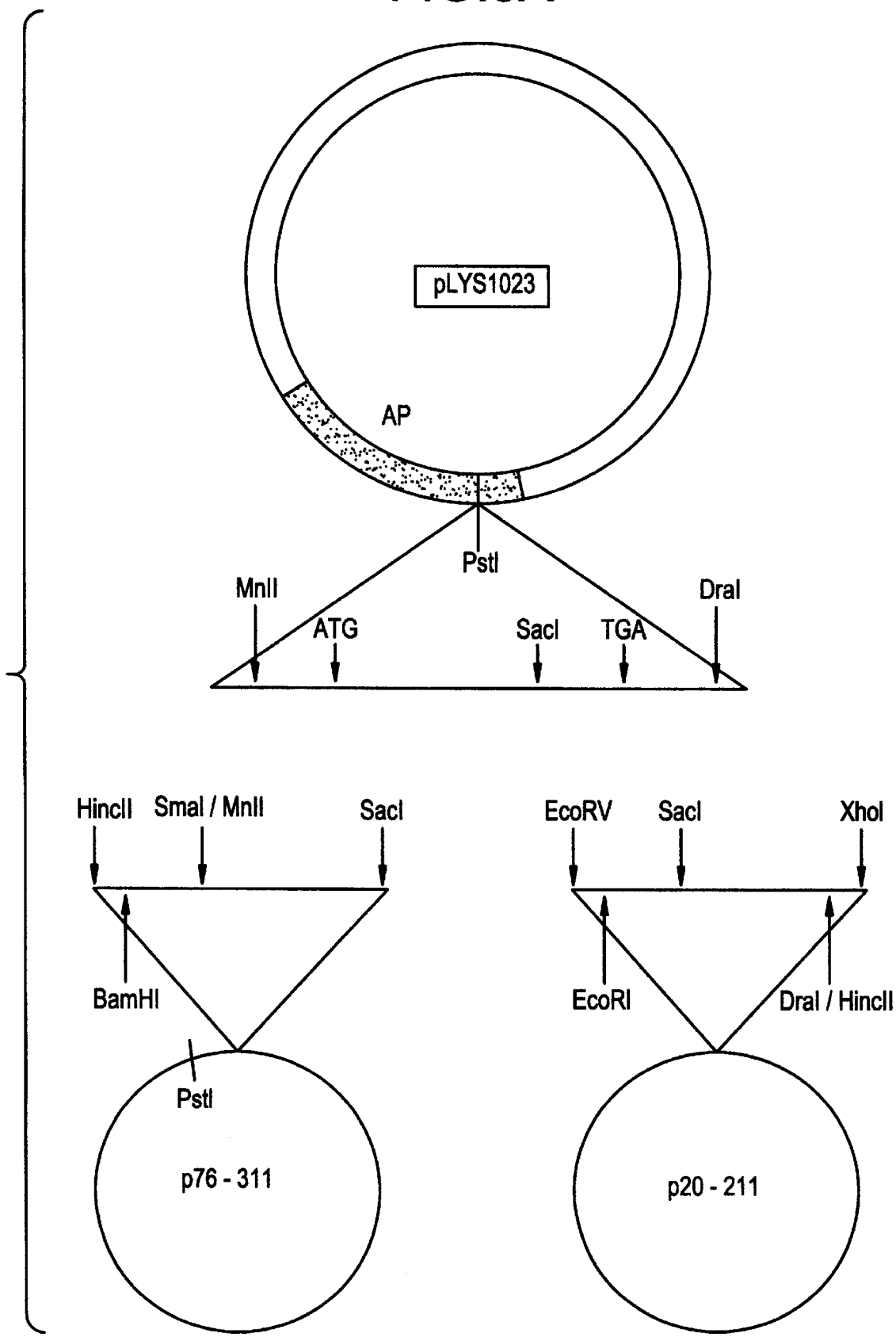
FIG. 5 is restriction maps of pLYS1023, p76–311, p20–211 and pCHLY.
Figure 5B:
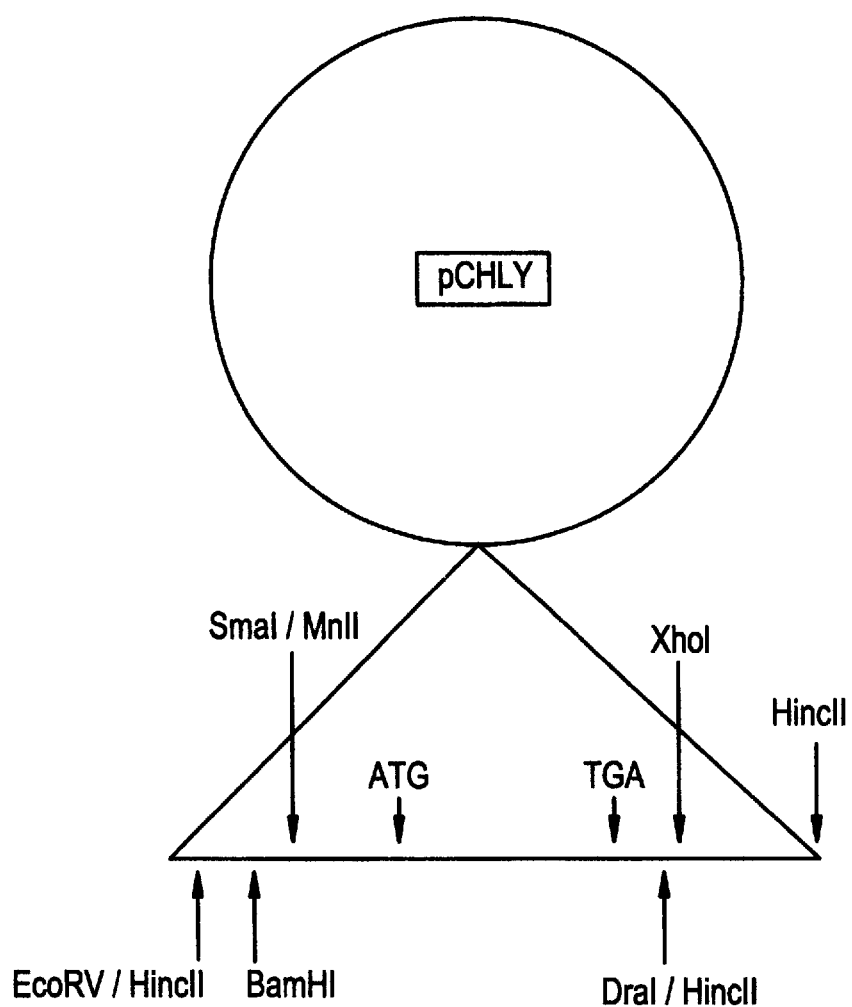

The plasmid pLYS1023 (FIG. 5) was digested with PstI and SacI. A 336 bp fragment was isolated and digested with MnlI to obtain the MnlI-SacI 311 bp fragment. This was ligated into pIBI76 between the SacI and SmaI sites. The resulting plasmid was designated p76–311 (FIG. 5). pLYS1023 was then digested with SacI and PstI, and a 252 bp fragment was isolated. This fragment was then digested with DraI and the SacI-DraI 211 bp fragment was isolated from agarose gel. The 211 bp fragment was then ligated into pIBI20 between the SacI and HincII sites, and the resuting plasmid was designated p20–211. p20–211 was digested with EcoRV and SacI and the fragment was purified from gel. This fragment was then ligated with the HincII-SacI 326 bp fragment from the p76–311 also purified from a gel, to obtain a plasmid designated pCHLy. The lysozyme gene (549 bp) was rescued from pCHLy with BamHI and XhoI and ligated into pMON530 between the BglII and XhoI sites to obtain pMONCHLy. The lysozyme gene is then cut from pMONCHLy and placed in pCAMV2X as described in Example 1. This plasmid is then cloned in E. coli and conjugated with A. tumefaciens which is then cultured with tobacco leaf discs also as described in Example 1. Callus eventually develops, and plants regenerated therefrom express the lysozyme gene and are resistant to P. syringae.

EXAMPLE 6

The lysozyme gene and protein was obtained from Hyalophora-derived plasmid pBR322, provided by Kleanthis Xanthopoulos. The lysozyme gene was removed from the plasmid pBR322 by digestion with the enzyme PstI. The resultant fragment was purified and treated with the Bal31 enzyme to remove the 3' poly dG tail. Then the adapter shown as follows:

GTTTCATGAAACAGATCTGTCGACA-
GATCTGTTTCATGAAAC

CAAAGTACTTTGTCTAGACAGCTGTCTA-
GACAAAGTACTTTG was ligated to the fragment after digestion with enzyme XmnI. Then the fragment was digested with SalI and cloned into the plasmid pBR322. The lysozyme gene was rescued by digestion with enzyme Bgl II and inserted into the plant vector pMON237. The plasmid pMON237 is similar to pMON530 except that it has the 19s promoter instead of the 35s, and has only the BglII and EcoR1 restriction sites near bp O. The procedure of Example 1 is then followed to place the lysozyme gene in pCAMV2X and to obtain plant transformants.

EXAMPLE 7

The antibacterial protein-producing cecropin gene, obtained in plasmid pBR322 received from Kleanthis Xanthopoulos was first cut with restriction enzymes PstI and HinPII to provide a plasmid fragment pCPFL1. The resulting 260 base pair fragment was purified and treated with T4 DNA polymerase to fill in the HinPII site. The resultant fragment was then treated with T4 DNA ligase and the synthetic adapter C3, which is identified as follows:

CTAGCATAAAGATCTGACGTCAGATCTTTATCCTAG

GATCGTATTTCTAGACTGCAGTCTAGAAATAGGATC, was joined to the fragment. The new gene fragment was then ligated to pBR322 which had been cleaved with restriction enzymes XmnI and AatII. Clones containing the correct ampicillin sensitive genotype were selected, cut with XmnI and ligated with a synthetic adaptor identified as C5, which has the following nucleotide sequence:

CTTTCCATTTCATGGTAGATCTACCATGAAATGGAAAG

GAAAGGTAAAGTACCATCTAGATGGTACTTTACCTTTC

The resultant fragment was retransformed into E. Coli. The cecropin gene is rescued from E. Coli by digestion with BglII and inserted into the plant vector pMON237. Thus, the cecropin gene is regenerated without its leader peptide and with an appropriate start methionine at the amino terminus end and the correct translational termination (stop) signal at the carboxy terminus end.

EXAMPLE 8

In vitro procedures utilizing a 41 base DNA oligonucleotide having the sequence:

GATCTCCACGGTTGTGGCCATATAATCATCGTGTTTTTCAA effectively blocked 98% of the translation of a virus genome. This procedure was carried out by hybridizing the DNA to the virus in an 8 microliter reaction mixture containing 20 mM Hepes, pH 7.6, 0.1M NaCl and 1 mM ETDA. RNA concentration of the virus was 0.5 $\mu$g/ml and the DNA was added in a five-fold molar excess. In general, the reaction mixtures were heated at 70° C. for 10 minutes followed by incubation at 45° C. for 3 hours. The process of determining viral RNA translation is in a cell-free protein synthesis regime, such as in RMA rabbit reticulocyte lysate system described in Shih et al, Proceedings of the National Academy of Science of the U.S.A., vol. 75, pp. 5807–5811 (1978) and in Journal of Virology, vol. 30, pp. 472–480 (1979), both of which are incorporated by reference as if fully set forth. As a result of the hybridization, viral translation of Tobacco mosaic virus was effectively blocked.

EXAMPLE 9

In the case of viroids, replication was prevented in the potato spindle tuber viroid (PSTV) by hybridization of synthetic DNA fragments to the PSTV in the central conserved region which appears to be present in all known viroids and is presumed to be important for replication. The synthetic DNA fragments have the oligonucleotide sequence and identification as follows:

GATCTAGGGATCCCCGGGGAAACCT PSTV1

GATCTAGGTTTCCCCGGGGATCCCT PSTV2

This hybridization was carried out by annealing the various oligonucleotide fractions to purified, infectious PSTV RNA. The sample mixture was heated to 90° C. for 5 minutes and then allowed to cool slowly to room temperature. These mixtures were then inoculated onto PSTV sensitive tomato plants and symptoms were allowed to develop. The results are shown in the Table below.

Table of Molar Ratio of Compositions Inoculated in Tomato Plants

| Innocula | Molar Ratio | Infected Tomato Plants (#infected/#innoculated) |
|---|---|---|
| PSTV + PSTV1 | 1:1 | 0/4 |
| PSTV + PSTV1 | 10:1 | 0/4 |
| PSTV + PSTV1 | 1:10 | 0/4 |
| PSTV + PSTV2 | 1:1 | 0/4 |
| PSTV + PSTV2 | 10:1 | 2/4 |
| PSTV + PSTV2 | 1:10 | 0/4 |
| PSTV + PSTVf* | 1:1 | 1/4 |
| PSTV + PSTVf | 10:1 | 0/4 |
| PSTV + PSTVf | 1:10 | 0/4 |
| PSTV alone |  | 3/5 |

*PSTV is a full length DNA of PSTV.

When hybridization occurs, the further replication of the PSTV molecule was blocked.

The synthetic DNA transcription blocking for viroids and synthetic DNA translation blocking for viruses are further inserted into the plant vector pCAMV2X and *A. tumefaciens* to produce tobacco plants which demonstrated expression by Southern blotting.

EXAMPLE 10

The pCAMV2X of Example 1 is used to transform rice plants (*Oryza sativa*). An aqueous solution of 100 μg/ml pCAMV2X is injected with a tuberculin syringe above each tiller node until several drops of the solution comes out of the tiller (about 300 μl). The plants are injected when the young tillers have 5 leaves, the flag leaf is about one-third to one-half its normal size and they contain a young influorescence of about 2 cm suitable for injection. This corresponds to about 14 days pre-meiosis. The plants are self-pollinated or cross-pollinated with other treated plants and the floral tillers grown to maturity.

The seeds from these plants are then surface sterilized and germinated in glass containers having about 400 ml of Knop nutritive solution supplemented with kanamycin sulfate at 10 μg/ml. About 10 seeds are positioned in a plastic net over the solution so that they are just in contact therewith. The seeds are maintained in a culture room at about 26° C. and receive about 2000 lux for 16 hours per day. Control seeds germinated in the kamaycin nutritive solution are albino after about 10 days. From about 3000 seeds obtained from the injection of 100 plants, about 3–15 remain green after 10 days. Approximately one-third of these plants show expression of the attacin gene by blotting techniques and have enhanced resistance to blast.

The procedure is repeated with the plasmids described in Examples 2–9 with similar results.

EXAMPLE 11

Protoplasts of rice are treated with pCAMV2X of Example 1 to obtain disease-resistant plants. Calli are cultured on a gyrating shaker at 27° C. in the dark in a suspension of medium B5 supplemented with 1 mg/l 2,4-dichlorophenoxy-acetic acid and 30 g/l sucrose, and subcultured twice a week by a 1:3 dilution with fresh medium. Protoplasts are isolated the second or third day following subculturing by sedimenting and incubating in a cell wall digestive solution containing 1% Onozuka Cellulase RS, 0.5% Macerozyme R10, 0.05% Pectolyase Y23, 0.6M mannitol and 5 mM $CaCl_2$ at pH 5.7. Following incubation at 27° C. for three or four hours, protoplasts are separated from the solution by filtering through a series of 100, 50 and 25 μm stainless steel sieves, and repeated centrifugations with sea water at 700 mOsmol/kg $H_2O$.

The protoplasts are resuspended at about $2 \times 10^6$/ml in medium F, and one ml of protoplast suspension is mixed with 0.4 ml of medium F containing 40% (w/v) polyethylene glycol 1500 and 10–50 μg pCAMV2X. This mixture is incubated in a laminar flow hood at 22°–24° C. for 30 minutes, diluted stepwise over a period of 20 minutes with medium F and protoplasts are collected by sedimentation in sea water and culture medium at 1:1 (v/v). The protoplasts are resuspended at $2-4 \times 10^5$ protoplasts/ml in medium C8/IV, and placed in 2 ml aliquots in 5 $cm^2$ dishes maintained at 27° C. in the dark. About 5–7 days later, the same volume of 1.2% agarose is added to the dish. The solidified medium is placed in a larger dish to which is added 20 ml of B5-1 medium containing 100 mg/l kanamycin sulfate. The liquid medium in the resulting bead-type culture is replaced every 10 days with fresh medium containing the antibiotic. Proliferating colonies are transferred to agar-solidified B5-1 medium with 100 mg/l kanamycin sulfate about two months later. The cells express the attacin gene as shown by standard blotting techniques, and plants regenerated therefrom have superior resistance to blast relative to control plants.

This procedure is repeated with the plasmids of Examples 2–9 with similar results.

EXAMPLE 12

Protoplasts of rice are prepared as described in the foregoing Example 11, and suspended at $1 \times 10^7$/ml in 0.5 ml PBS. The mixture is heat shocked for five minutes at 45° C. and cooled on ice to room temperature. First, the plasmid pCAMV2X of Example 1, and then polyethylene glycol, are added to the mixture at 10–50 μg/ml and about 8% w/v, respectively. Following incubation for 5 minutes, the mixture is transferred to the chamber of a BIO-RAD electroporator equipped with an ISCO 494 power supply. The power supply is connected to the shock chamber, and set at 2000 V and 0.9 mA limit. The wattage and current dials are set to 5% and the power supply (capacitor) is discharged. The electroporated protoplasts are then maintained at 20° C. for about 10 minutes and diluted with growth medium and agar to form a bead type culture. The protoplasts are cultured at 24° C. in the dark for one day and in 500 lux continuous light for 6 days. The protoplasts are then cultured in the same medium containing 50 mg/l kanamycin sulfate as described in Example 11. Similar results are observed, except the transformation efficiency is higher.

EXAMPLE 13

The following DNA sequence was synthesized on an Applied Biosystems DNA synthesizer:
A A G C T T G A T C C A A C A A T G G A A A A A T G -
G A T G A A A G A A A T C T G G A A A G T G C T T A A A -
G A T A T G A T C G A T A A A A T G A A A A C T T T C A
C T A G G T T G T T A C C T T T T T A C C T A C T T T C T T T A G A C C -
T T T C A C - G A A T T T C T A T A C T A G C T A T T T-
T A C T T T T G A A A G T GATACTCTTTTCGAAATGATCAC-
TAAACTTTTCACTGAAGTCGAAAAATG-
GATGAAAGAAATCTGGAAAGTGCTTAAA
CTATGAGAAAAGCTTTACTAGTGATTTGAAAAGTG-
ACTT- CAGCTTTTTACCTACTTTCTTTAGTC-
CTTTCACGAATTT
GATATGATCGATAAAAT-
GAAAACTTTCGTGGATACTCTTTTC-
GAAATGTGGACTAAAGTGCTTACT-
GAAGTGGAAAAA
CTATACTAGATATTTTACTTTTGAAAG-
CACCTATGAGAAAAGCTTTACACCT-
GATTTCACGAATGACTTCACCTTTTT
TGGATGAAAGAAATCTGGAAATTCCT-
TAAAGATATGATCGATAAAAT-
GAAAACTTTCTGGGATACTCTTCTTGAAATG
ACCTACTTTCTTTAGACCTTTAAG-
GATTTCTATACTAGCTATTT-
TACTTTTGAAAGACCCTATGAGAAGAACTTTAC
ATCACTAAATGGTTCACTGAAGTG-
GAAAAATGGATGAAAGAAATCTG-
GAAAGTGCTTAAAGATATGATCGATAAAATG
TAGTGATTTACCAAGTGACTTCACCTTTTTACCTAC-
TTTC- TTTAGACCTTTCACGAATTTCTATAC-
TAGCTATTTTAC
TGAGGATC
ACRCCTAGTTCGAA This DNA sequence is then inserted into the HindIII site of pCAMV2X, and used to transform potatoes using an *A. tumefaciens* vector. The resulting potatoes express the protein

MFKWMKEIWKVLKDMIDKMKTFIDTLFEM

ITKLFTEVEKWMKEIWKVLKDMIDKMKTFVDTLFEM

LEMITKWFTEVEKWMKEIWKVLKDMIDKM and have a relatively high essential amino acid content.

EXAMPLE 14

The foregoing Examples 1–9 and 13 are repeated sequentially with potatoes to obtain a potato with a wide spectrum of microbial resistance to bacteria, fungi, viruses and viroids and enhanced limiting essential amino acid content. First, potato leaf discs are used instead of tobacco according to the procedure of Example 1. Transformants obtained thereby are then treated with a pCAMV2X vector similar to that of Example 2 except that a different antibiotic resistance marker is present in the plasmid construct for selection of transformants. Transformants expressing the antimicrobial genes of Examples 1 and 2 are then sequentially transformed in the same manner with the vectors of Examples 3–9 and 13, using a different selectable marker in each transformation stage. The resulting potato plants express attacin, lysozyme, cecropin, and the protein of Example 13, and have resistance to a wide spectrum of bacteria, fungi and viruses, as well as an enhanced essential amino acid content.

EXAMPLE 15

The procedure of Example 14 is followed, except that rice is used instead of potatoes, and the electroporation of rice protoplasts described in Example 12 is used instead of the Agrobacterium vector. The resulting rice plants have a similar microbial resistance and enhanced nutritional quality.

EXAMPLE 16

The nucleotide sequence and polypeptide sequence of some synthetic polypeptide genes are designated Sp44 and Sp47. These genes were constructed symmetrically so that the correct reading frame is maintained in either direction. Hence, there are two possible polypeptides for each synthetic gene.

Single strand DNA sequences were constructed via an automated DNA synthesizer which uses a solid support phosphite synthesis method of the triester method of synthesis. The following synthetic oligonucleotides were constructed: 5'(AAGAAATGGATG)3', 5'(CATCCA)3', 5'(TTTCTT)3', 5'(ACGATC)3', 5'(GATCGT)3', and 5'(CCCGAATTCGGG)3'. The synthetic oligodeoxynucleotides were phosphorylated in the terminal 5'-OH position by the action of T4 polynucleotide kinase. The labeled oligodeoxynucleotides were added to a final volume of 25 $\mu l$ with the following molar concentrations: AAGAAATGGATG, TTTCTT, and CATCCA were at 61 $\mu M$ each and ACGATC and GATCGT were at 40 $\mu M$ each. The sequence containing the EcoR1 recognition sequence was at a concentration of 2.4 $\mu M$. This mixture was boiled for 2 minutes and cooled to room temperature for over a period of 3 hours. Ligation buffer was added followed by the enzyme T4 DNA ligase and the resultant mixture incubated at 13° C. overnight. Following ligation, the synthetic genes were precipitated with ethanol, redissolved in water and digested wtih EcoR1. After digestion the sample was passed over a Sephadex G-75 column in order to separate the small molecular weight linked fragments from the synthetic genes. The high molecular weight fractions were pooled, precipitated and ligated with EcoR1-digested pBR325. Competent *E. coli* strain RR1 cells were transformed with the above ligation mixture. Approximately 45 clones which were ampicillin-resistant and chloramphenicol-sensitive were obtained from one ligation. Two recombinant DNA strains designated Sp44 and Sp47 were selected for DNA sequence analysis by the method of Sanger.

As a result of the sequence analysis, the nucleotide sequence and amino acid composition of the peptide identified as Sp47 and the peptide identified as Sp44 were determined and are set forth below.

Sp47
NUCLEOTIDE SEQUENCE AND AMINO ACID COMPOSITION

SP47 (1)
AATTCGGGGATCGTAAGAAATGGATGGATCGTCATCCATTTCTTCATCCATTTCTTACGATCCATCCATTTCTT
GCCCCTAGCATTCTTTACCTACCTAGCAGTAGGTAAAGAAGTAGGTAAAGAATGCTAGGTAGGTAAACAA
AAGAAATGGATGAAGAAATGGATGACGATCCATCCATTTCTTCATCCATTTCTTCATCCATTTCTTACCATCAA
TTCTTTACCTACTTCTTTACCTACTGCTACGTAGGTAAAGAAGTAGGTAAAGAAGTAGGTAAAGAATGCTAGTT
GAAATGGATGAAGAAATGGATGAAGAAATGGATGAAGAAATGGATGCATCCATTTCTTAAGAAATGGATGAAGA
CTTTACCTACTTCTTTACCTACTTCTTTACCTACTTCTTTACCTACGTAGGTAAAGAATTCTTTACCTACTTCT
AATGGATGAAGAAATGGATGACGATCGATCGTAAGAAATGGATGACGATCCATCCATTTCTTACGATCCCCG

-continued

TTACCTACTTCTTTACCTACTGCTAGCTAGCATTCTTTACCTACTGCTAGGTAGGTAAAGAATGCTAGGGGCTTAA

SP47

SP47 (1)
GDRKKWMDRHPFLHPFLTIPFLKKWMKKWM
TIHPFLHPFLHPFLTIKKWMKKWMKKWMHPF
LKKWMKKWMKKWMTIDRKKWMTIHPFLTIP

SP47 (2)
GlyAspArgLyslysTrpMetAspArgHisProPheLeuThrIleAspArglHisProPheLeuHis
ProPheLeuHisProPheLeuLysTrpMetHisProPheLeulHisProPheLeulHisProPheLeuHis
ProPheLeuAspArgLysLysTrpMetLysLysTrpMetLysLysTrpMetAspArgHisProPheLeuHis
ProPheLeuLysLysTrpMetAspArgLysLysTrpMetLysLysTrpMetThrIlelHisProPheLeuThr
IlePro

|       |     | ARG | ASP | GLY | HIS  | ILE  | LEU  | LYS  | MET  | PHE  | PRO  | THR |
|-------|-----|-----|-----|-----|------|------|------|------|------|------|------|-----|
| SP47  | (1) | 3   | 3   | 1   | 8    | 6    | 8    | 22   | 11   | 8    | 9    | 6   |
|       | %   | 3.1 | 3.1 | 1.0 | 8.3  | 6.3  | 8.3  | 23.0 | 11.5 | 8.3  | 9.4  | 6.3 |
| SP47  | (2) | 6   | 6   | 1   | 11   | 3    | 11   | 16   | 8    | 11   | 12   | 3   |
|       | %   | 6.3 | 6.3 | 1.0 | 11.5 | 3.1  | 11.5 | 16.7 | 8.3  | 11.5 | 12.5 | 3.1 |

Mol. Wt.

SP47 (1)  14,322Da
SP47 (2)  14,232Da

SP 44
NUCLEOTIDE SEQUENCE AND AMINO ACID COMPOSITION

AATTCGGGACGATCACGATCCATCCATTTCTTAAGAAATGGATGACGATCCATCCATTTCTTAAGAAATGGATG
    GCCCTGCTAGTGCTAGGTAGGTAAAGAATTCTTTACCTACTGCTAGGTAGGTAAAGAATTCTTTACCTAC
ACGATCCATCCATTTCTTCCCG
TGCTAGGTAGGTAAAGAAGGGCTTAA

SP44 (1)
GTITIHPFLKKWMTIHPFLKKWMTIHPFLP

SP44 (2)
GlyLysLysTrpMetAspArfHisProPheLeuLysLysTrpMetAspArgHisProPheLeuLysLys
TrpMetAspArgAspArgPro

|      |     | ARG  | ASP  | GLY | HIS  | ILE  | LEU  | LYS  | MET | PHE | PRO  | THR  | TRP |
|------|-----|------|------|-----|------|------|------|------|-----|-----|------|------|-----|
| SP44 | (1) | 0    | 0    | 1   | 3    | 4    | 3    | 4    | 2   | 3   | 4    | 4    | 2   |
|      | %   | 0    | 0    | 3.3 | 9.9  | 13.3 | 9.9  | 13.3 | 6.6 | 9.9 | 13.3 | 13.3 | 6.6 |
| SP44 | (2) | 4    | 4    | 1   | 2    | 0    | 2    | 6    | 3   | 3   | 3    | 0    | 3   |
|      | %   | 13.3 | 13.3 | 3.3 | 6.6  | 0    | 6.6  | 20.0 | 9.9 | 9.9 | 9.9  | 0    | 9.9 |

In order to determine the amount of type of polypeptide produced by the recombinant cells, *E. coli* cells retaining the plasmids were grown in M9 media supplemented with 0.5% casamino acids and 1.0 g. per ml thiamine, at 37° C. Ten mls of each culture was placed in 100 mls of the supplemented M9 medium and grown again at 37°. After this time approximately 10 $\mu$Ci each of $^3$H lysine and $^{35}$S cysteine were added to the cells and 1 ml was withdrawn hourly and the amount of label incorporated into the polypeptide were determined. The recombinant microbes used contained Sp47 and Sp44 genes on the plasmid pBR325. The control was a bacteria which contained pBR325 alone. Hourly 1 ml samples were withdrawn and the counts incorporated into polypeptide determined. The ratio ($^3$H lysine/$^{35}$S cysteine) of uptake was substantially higher in cells that contained pSP44 and pSP47 plasmids than those with pBR325. This indicates that polypeptides with higher levels of lysine are being synthesized by bacteria containing the recombinant plasmids pSP44 and pSP47.

Figure 11:
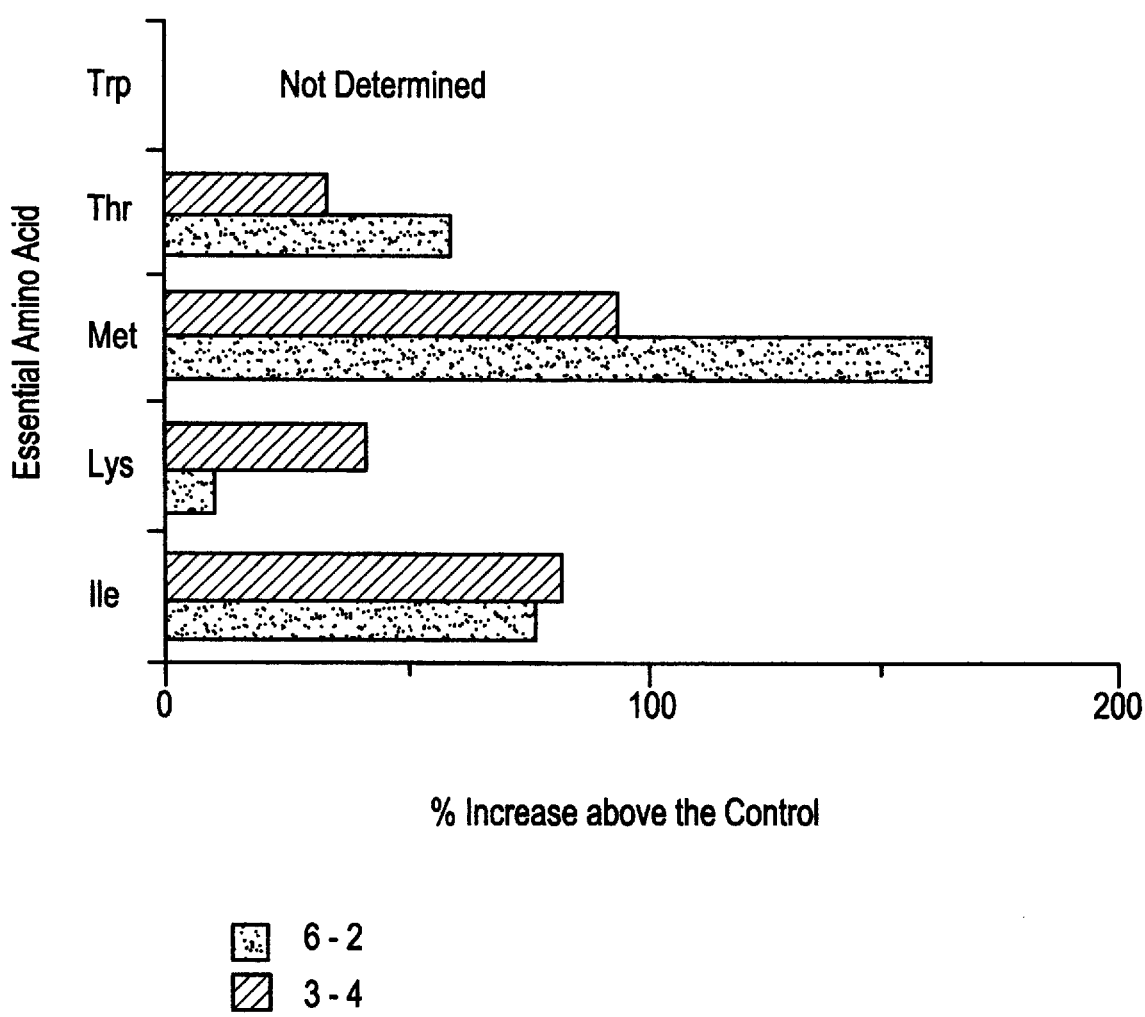
FIG. 11 is a graph illustrating the enhancement of essential amino acid content of the lotononis transformants of Example 16.

The pSP47(2) plasmids were inserted into lotononis using an Agrobacterium vector. Plants selected at random had increased essential amino acid levels as indicated in FIG. 11.

Having described the invention above, many variations from the illustrated details will occur to those skilled in the art. It is intended that all such variations within the scope and spirit of the appended claims be embraced thereby.

What is claimed is:

1. A plant having an expressible heterologous gene encoding a polypeptide or a protein comprising at least 25–60 percent by weight of limiting amino acids, the polypeptide or protein being stable toward plant proteases and digestible by animal proteases.

2. The plant of claim 1 wherein the limiting amino acids are selected from the group consisting of lysine, tryptophan, methionine, threonine and isoleucine.

3. A plant comprising an expressible heterologous gene encoding a protein comprising the amino acid sequence G D R K K W M D R H P F L H P F L T I P F L K K W - M K K W M T I H P F L H P F L H P F L T I K K W M K K W - MKKWMHP FLKKWMKKWMKKWMTIDRKKWMTI- HPFLTIP.

4. A plant comprising an expressible heterologous gene encoding a polypeptide comprising the amino acid sequence GTITIHPFLKKWMTIHPFLKKWMTIHPFLP.

5. A plant having an endogenous protein content having a limiting amino acid content, comprising an expressible heterologous gene encoding a polypeptide or a protein comprising at least 25–60 percent by weight of limiting amino acids, the polypeptide or protein being stable toward plant proteases and digestible by animal proteases, wherein the polypeptide or protein encoded by the heterologous gene represents a profile of limiting amino acids that supplements the limiting amino acid content of the endogenous protein of the plant such that the overall content of at least one limiting amino acid is increased with respect to the level of that amino acid in the plant's endogenous protein alone.

6. The plant of claim 5 wherein the limiting amino acids of the polypeptide or protein are selected from the group consisting of lysine, tryptophan, methionine, threonine and isoleucine.

* * * * *